(12) United States Patent
Agami et al.

(10) Patent No.: US 7,241,618 B2
(45) Date of Patent: Jul. 10, 2007

(54) EXPRESSION SYSTEM

(75) Inventors: Reuven Agami, Amsterdam (NL); Thijn Brummelkamp, Amsterdam (NL)

(73) Assignee: Cancer Research Technology Limited, London (GB)

( * ) Notice: Subject to any disclaimer, the term of this patent is extended or adjusted under 35 U.S.C. 154(b) by 157 days.

(21) Appl. No.: 10/324,184

(22) Filed: Dec. 19, 2002

(65) Prior Publication Data

US 2003/0144239 A1 Jul. 31, 2003

Related U.S. Application Data

(63) Continuation-in-part of application No. 10/216,054, filed on Aug. 9, 2002, now abandoned.

(30) Foreign Application Priority Data

Dec. 24, 2001 (GB) .................... 0130955.8

(51) Int. Cl.
*A61K 31/70* (2006.01)
*C07H 21/04* (2006.01)
*C07H 21/02* (2006.01)
*C12N 5/00* (2006.01)

(52) U.S. Cl. .................. 435/325; 435/6; 435/320.1; 536/23.1; 536/24.5; 514/44

(58) Field of Classification Search .................. None
See application file for complete search history.

(56) References Cited

U.S. PATENT DOCUMENTS 5,624,803 A * 4/1997 Noonberg et al. ............. 435/6
2003/0148519 A1 * 8/2003 Engelke et al. ............. 435/455
2004/0002077 A1 1/2004 Taira et al.

FOREIGN PATENT DOCUMENTS

WO WO 03/006477 A1 1/2003
WO WO 03/020931 A2 3/2003
WO WO 03/022052 A1 3/2003
WO WO 03/046173 A1 5/2003

OTHER PUBLICATIONS

Elbashir et al. Functional anatomy of siRNAs for mediating efficient RNAi in *Drosophila melanogaster* embyro lysate (2001) The EMBO Journal, vol. 20(23):pp. 6877-6888.*
Ui-Tei et al. Sensitive assay of RNA interference in *Drosophila* and Chinese hamster cultured cells using firefly luciferase gene as target. 2000 FEBS Letters vol. 479: pp. 79-82.*
Caplen, N. RNAi as a gene therapy approach. Expert Opin. Biol. Ther. 2003, vol. 3, p. 575-586.*
Zhang et al. Current Pharmaceutical Biotechnology 2004, vol. 5, p. 1-7.*
Check, E. Nature, 2003, vol. 425, p. 10-12.*
Agrawal et al. Molecular Medicine Today 2000 vol. 6, p. 72-81.*
Agami, "RNAi and Related Mechanisms and Their Potential Use for Therapy," *Current Opinion in Chemical Biology*, 6:829-834, Elsevier Science Ltd. (2002).
Bass, "The Short Answer," *Nature*, 411:428-429, Macmillan Magazine Ltd. (2001).
Brummelkamp et al., "Stable Suppression of Tumorigenicity by Virus-Mediated RNA Interference," *Cancer Cell*, 2:243-247, Cell Press (2002).
Brummelkamp et al., "A System for Stable Expression of Short Interfering RNAs in Mammalian Cells," *Science*, 296:550-553 (2002).
Elbashir et al., "Duplexes of 21-Nucleotide RNAs Mediate RNA Interference in Cultured Mammalian Cells," *Nature*, 411:494-498, Macmillan Magazines Ltd. (2001).
Tuschl, "Expanding Small RNA Interference," *Nature Biotechnology*, 20:446-448, Nature Publishing Group (2002).

* cited by examiner

*Primary Examiner*—Sean McGarry
(74) *Attorney, Agent, or Firm*—DLA Piper US LLP

(57) ABSTRACT

The present invention provides a polynucleotide comprising a RNA polymerase III promoter, a region encoding a siRNA, and a transcriptional termination element comprising five consecutive thymine residues. The invention also provides for vectors, cells and non-human transgenic animal comprising the polynucleotides of the invention as well as their use in medicaments for various conditions.

16 Claims, 14 Drawing Sheets

EXPRESSION SYSTEM

This application is a continuation-in-part of U.S. Ser. No. 10/216,054, filed Aug. 9, 2002, now abandoned, the entire content of which is incorporated herein by reference.

BACKGROUND OF THE INVENTION

1. Field of the Invention

This invention relates to a polynucleotide or vector for expressing short interfering RNAs (siRNAs) to inhibit the expression of a target gene. The invention also relates to cells and non-human transgenic animals comprising the polynucleotide or vector and their various uses including in target drug validation and in human therapeutics.

The ability to inhibit or disrupt the function of a specific gene is highly desirable both from the point of view of studying gene function and also from a therapeutic perspective.

Many diseases arise from either the expression of a mutated gene or from abnormal, and in particular elevated or inappropriate, expression of a particular gene. Such mutations may be inherited, such as in the case of autosomal dominant disorders, or occur in the somatic or germ line tissues of an individual, such as in the case of cancer. The ability to modulate the expression of a mutated allele or of an inappropriately expressed wild type allele in various diseases or disorders may therefore be used to provide therapies to treat the disorders. In addition, in various infectious diseases, such as viral infection, the ability to inhibit the expression of viral genes in the host cell, or of a gene encoding a host cell protein involved in the life cycle of the virus, may also lead to possible treatments for infectious diseases.

The ability to inhibit gene expression has also been used to study gene function. Techniques such as classical mutagenesis have provided great insights into gene function, but such techniques are labour intensive, expensive and may take long periods of time. Such techniques simply may not be practical in higher organisms and require a means to identify the desired mutant. They also do not offer the possibility of mutating a specific gene of choice.

Although various methods for targeted gene disruption have been developed, where a gene of choice can be inhibited or disrupted, these also suffer from limitations. Techniques such as gene targeting are highly costly, expensive and time consuming often taking several years to obtain a homozygous mutant. Gene targeting also requires detailed knowledge of the structure of the gene to be disrupted.

As well as gene targeting antisense technology has also been developed to try and disrupt a specific gene. However, antisense RNA is unstable and it is often difficult to achieve high enough levels of antisense RNA in cells to achieve effective inhibition of a target gene.

Recently, it has been found in organisms such as *C. elegans, Drosophilia melanogaster* and plants that double stranded RNA molecules (dsRNA) are capable of inhibiting the expression of a target gene that they share sequence identity or homology to. The observed phenomena, sometimes referred to as post transcriptional gene silencing (PTGS), are thought to represent a possible cellular defence mechanism against viruses or transposons. Typically, in the studies carried out in these organisms the dsRNA has been introduced into cells by techniques such as microinjection or transfection and the inhibition of a target gene such as a reporter gene been measured.

The mechanism by which the dsRNA exerts its inhibitory effect on the target gene has begun to be elucidated. It is thought that the dsRNA is processed into duplexes of from 21 to 25 nucleotides in length. These short duplexes have been detected in plants where PTGS is occurring as well as in extracts of *D. melanogaster* schenider-2 (S2) cells transfected with a dsRNA molecule. It has been found that the processing reaction of a dsRNA can be carried out in vitro using extracts from these S2 cells. This provides an in vitro model system in which both the processing, targeting and transcript cleavage mechanisms involved in gene silencing can be studied. In the S2 lysate it was observed that the target mRNA was cleaved at 21 nucleotide intervals and that synthetic 21 and 22 RNA duplexes added to the lysate were able to guide efficient sequence specific mRNA degradation. Larger duplexes of 30 bp dsRNA were found to be active. The 21 nucleotide RNA products in the system were therefore named small interfering or silencing RNAs (siRNAs).

Factors from the target cell are also necessary for gene silencing. In *D. melanogaster* a ribonuclease III enzyme, dicer, is required for processing of the long dsRNAs into siRNA duplexes. It is thought that genes homologous to dicer exist in other organisms including mammals and humans as well as homologs or counterparts to the other host factors necessary. The initial steps in silencing involve the generation of a siRNA containing endonuclease complex. The endonuclease may be dicer or a gene homologous to dicer. The complex then specifically targets the mRNA transcript by a mechanism involving the exchange of one of the strands of the siRNA duplex with the region of sequence identity in the target transcript. Following this strand exchange, cleavage of the mRNA transcript occurs.

The cleavage of the target mRNA may occur at the ends of the duplexed region so, in effect, regenerating the siRNA endonuclease complex with one of the two strands of the regenerated siRNA coming from the original siRNA molecule and the other from the target transcript. Multiple cycles of transcript mRNA cleavage and hence siRNA regeneration may mean that each initial siRNA molecule can inactivate multiple copies of the target mRNA. Once the target mRNA transcript has been cleaved, the cleavage products not in the regenerated siRNA are rapidly degraded as they either lack the stabilising cap or pol(A)tail.

Although experiments investigating gene silencing in lower organisms have offered promising results it is thought that they may not be applicable to higher organisms such as mammals. It is thought that in higher organisms, such as mammals, cellular defence mechanisms operate which are triggered by dsRNA. It is believed that dsRNAs activate the interferon response which leads to a global shut-off in protein synthesis as well as non-specific mRNA degradation. This can lead to cell death and hence prevent selective gene inhibition. The presence of such defence mechanisms means that the applicability of gene silencing employing dsRNA in higher organisms has been questioned.

Experiments which have claimed to have demonstrated the efficacy of dsRNA in inhibiting the expression of a target gene in higher organisms have either been in non-mammalian systems, such as zebra fish or chicks, or alternatively in mammalian systems such as early embryos where the viral defence mechanisms are not thought to operate.

Preliminary experiments transfecting and/or microinjecting synthetic siRNAs, rather than longer dsRNA molecules which can be processed to give rise to a siRNA, have led to speculation that it might be possible to overcome the problems of the viral defence mechanisms in higher organisms. It may be that there is a threshold for the length of dsRNA necessary to activate the cell's defence mechanisms. The size of the synthetic siRNAs, and in particular the double stranded regions in them, introduced into the target cell may be small enough that they are below this threshold and hence do not activate the defence mechanisms.

SUMMARY OF THE INVENTION

It has now been found according to the present invention, that, by using a RNA polymerase III promoter, and in particular a type 3 RNA polymerase promoter, in combination with a transcriptional termination sequence comprising a string of five consecutive thymine residues in the sense strand that siRNAs can be efficiently expressed in animal cells and in particular in mammalian cells.

By using the RNA polymerase III promoter in conjunction with the transcriptional terminator this ensures that one of the 3' overhangs necessary for optimal inhibitory activity is present in the siRNA generated from the constructs of the invention. The second 3' overhang may be produced by cleavage of a stem loop structure in the transcript generated from the construct.

The fact that the constructs of the invention are DNA molecules capable of integrating into the genome of the target cell allows for stable, long term expression of the siRNA and hence long term inhibition of the target gene.

Accordingly, the present invention provides a polynucleotide comprising:
 a RNA polymerase III promoter;
 a region encoding a siRNA; and
 a transcriptional termination element comprising five consecutive thymine residues.
The invention also provides for
 a vector comprising a polynucleotide of the invention;
 a cell comprising a polynucleotide or vector of the invention;
 a non-human transgenic animal comprising a polynucleotide or vector of the invention;
 the use of a polynucleotide or vector of the invention to inhibit or reduce the expression of a target gene.

The invention also provides for a method of identifying an agent capable of modulating the phenotype of a cell or non-human transgenic animal of the invention, in a desired manner comprising determining whether a test agent can modulate the phenotype of the cell or transgenic organism in the desired manner.

The invention further provides for a method for identifying:
 (i) a modulator of transcription and/or translation of a target gene; and/or
 (ii) a modulator of the activity of a target polypeptide, in a cell or a non-human transgenic animal of the invention, which method comprises determining whether a test agent can modulate transcription and/or translation of the target gene or the activity of the target polypeptide.
The invention also provides:
 an agent or modulator identified by a method of the invention;
 a pharmaceutical composition identified by a method of the invention.
 a kit comprising a polynucleotide, vector, or cell of the invention and a means for detecting and/or quantifying the expression of the target gene;
 a pharmaceutical composition comprising a polynucleotide, vector, cell, agent or modulator of the invention and a pharmaceutically acceptable excipient;
 a polynucleotide, vector, cell, agent or modulator of the invention for use in a method of treatment of the human or animal body by therapy or diagnosis; and
 the use of a polynucleotide, vector, cell, agent or modulator of the invention in the manufacture of a medicament for the treatment or prevention of cancer or an autosomal dominant disorder.

BRIEF DESCRIPTION OF THE FIGURES

FIG. 1(a) shows a schematic drawing of the basic pSUPER vector. FIG. 1(b) depicts the synthetic siRNA used to target CDH1 and the predicted secondary structures of the three pSUPER-CDH1 transcripts (A, B and C) from each of the three pSUPER-Cdh1 constructs evaluated. FIG. 1(c) shows a western blot for Cdh1. The cell extracts on the blot are from cells transfected with (from left to right) a control plasmid expressing GFP, Cdh1-siRNA, the empty pSUPER construct, the three pSUPER constructs capable of expressing the transcripts A, B and C indicated in FIG. 1(b) and finally empty pSUPER. FIG. 1(d) shows a northern blot of RNA extracted from cells transfected with the various constructs indicated. The position of the stem loop and siRNA are indicated on the blot. The 5S-RNA band was also measured with Ethidium Bromide staining as a control for loading.

FIG. 5A shows a northern blot of RNA from MCF-7 cells transfected with pSUPER or the pSUPER-p53 vector. MCF-7 cells were electroporated with pSUPER-p53 or vector and total RNA was extracted 48 hours later. Thirty μg of RNA was separated on agarose gel, blotted and probed with a p53 specific $^{32}$P labeled probe. The rRNAs controls for loading were visualized by Ethidium Bromide staining of the blot. FIG. 5B shows siRNA interference mediated by the same stem-loop transcript can be expressed from retro viral vectors. Self-inactivating retro viral vectors (pRETRO-SUPER) expressing the puromycin marker gene were cloned to harbor either an empty pol-III promoter or one that targets p53 as depicted. U2-OS cells containing the Ecotropic-receptor were infected three times with these vectors and one day later cells were selected for 4 days with 1 μg/ml puromycin and plated on glass slides. One day later, slides were irradiated (20Gy), fixed four hours later and stained with anti-p53 antibody. Immuno-florescence with a FITC-conjugated secondary antibody is shown together with the phase contrast of the same field. Both pictures were taken using the same settings of the camera and microscope. FIG. 5(C) shows a schematic for pRETRO-SUPER with long terminal repeats (LTRs) at either end, a puromycin selectable marker with the H1 RNA gene promoter, target sequence and terminator also inserted.

FIG. 7A is a schematic drawing of retroviral pRETRO-SUPER RNA interference vector (pRS). DNA fragments containing the H1-RNA promoter with no insert or with an insert to target human p53 (as described in Example 2) were digested (EcoRI-XhoI) from corresponding pSUPER constructs and cloned into a self inactivating MSCV to generate pRS and pRS-p53, respectively. FIG. 7B shows immuno-stained cells. Human U2-OS cells that stably express the murine ecotropic receptor (to allow retorviral entry into cells) were infected with pRS and pRS-p53 retrovirus and selected for one week with puromycin. Polyclonal populations of puromycin-resistant cells were immuno-stained for p53 (in green) and for actin (in red). FIG. 7C shows a Western blot in which whole cell extracts were made from the same infected polyclonal populations of U2-OS cels as in FIG. 7B, separated by SDS-polyacrylamide gel electrophoresis (PAGE), and immunoblotted to detect p53 protein. FIG. 7D shows Northern blot analysis, in which 30 μg of total RNA from the same infected cell population described in FIG. 7B was preformed and probed with the sense 19 nucleotide targeting p53 sequence, as described in Example 2.

FIG. 8A shows the sequences of the wild type and V12 mutant alleles of human K-RAS and the predicted mutant-specific short hairpin transcript encoded by pSUPER-K-RAS$^{V12}$. FIG. 8B shows an immunoblot. The 19 nt sequence spanning the V12 mutation of K-RAS$^{V12}$ was used to generate a pSUPER-K-RAS$^{V12}$ (pS-K-RAS$^{V12}$) construct. This construct, an empty pSUPER (pS) and H2B-GFP plasmids were electroporated into CAPAN-1 cells and whole cell extracts were prepared as described in Agami, et al, *Cell* 102, 55–66 (2000)). Immunoblot analysis was preformed using a specific anti K-RAS antibody (sc-30, Santa Cruz) and anti cyclin-D1 as control. FIG. 8C shows a Western blot produced as follows. The pSUPER cassette, containing the K-RAS$^{V12}$ targeting sequence, was cloned into pRS as described in FIG. 7, and virus stock was produced. A stable polyclonal pool of CAPAN-1 cells that expresses the murine ecotropic receptor was infected with the indicated viral stocks. Cells were selected with puromycin for three days and whole cell extracts were used for immunoblot analysis to detect K-RAS protein and the controls p53 and actin. FIG. 8D shows a Western blot produced as follows. Stable polyclonal pools of CAPAN-1 and EJ cells that express the ecotropic receptor were infected with the indicated virus stocks, drug selected and immunoblotted to detect K-RAS, p53 and actin proteins.

FIG. 9A is one representative of three independent experiments in which $2 \times 10^4$ selected cells from the indicated infections were plated in duplicates in 2.5 cm diameter plates containing soft agar. FIG. 9B shows athymic mice into which $1 \times 10^6$ selected cells from pRS and pRS-K-RAS$^{V12}$ infections were injected subcutaneously as indicated. Four weeks later, mice were inspected for the presence of tumors at the site of injection.

BRIEF DESCRIPTION OF THE SEQUENCES

SEQ ID NO:1 provides the sequence for the human H1 RNA gene as available from GenBank under accession number X16612.

SEQ ID NO:2 provides the sequence for the preferred H1 RNA gene promoter and corresponds to from nucleotide 146 to nucleotide 374 of the sequence of SEQ ID NO:1.

Figure 1:
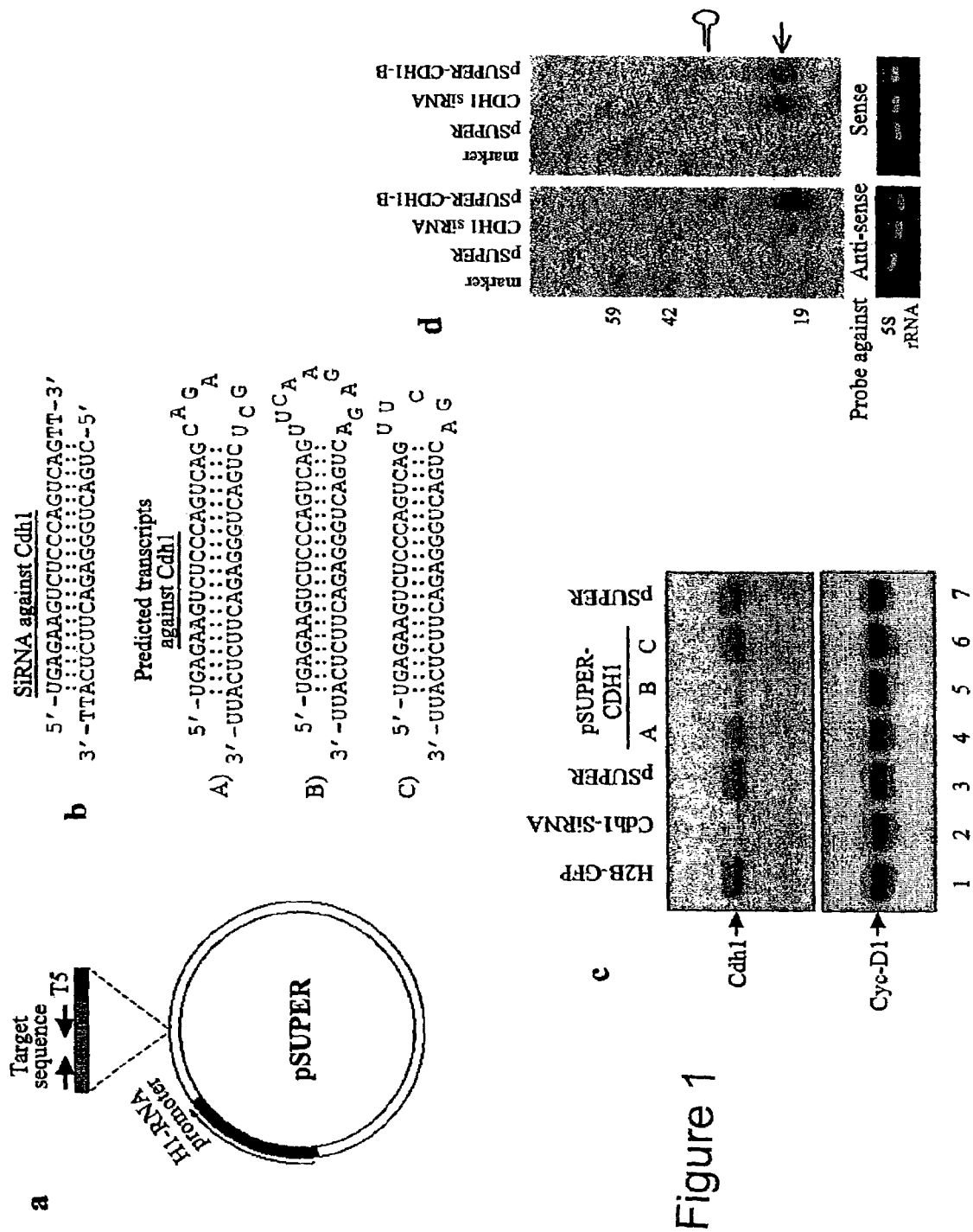
FIG. 1 shows suppression of gene expression in mammalian cells by a vector of the invention.

SEQ ID NO:3 provides the sequence of the sense strand of the synthetic siRNA against Cdh1 depicted in FIG. 1(b).

SEQ ID NO:4 provides the sequence of the antisense strand of the synthetic siRNA against Cdh1 depicted in FIG. 1(b).

SEQ ID NO:5 provides the sequence of the predicted stem loop transcript generated from pSUPER-Cdh11-A depicted in FIG. 1(b).

SEQ ID NO:6 provides the sequence of the predicted stem loop transcript generated from pSUPER-Cdh11-B depicted in FIG. 1(b).

SEQ ID NO:7 provides the sequence of the predicted stem loop transcript generated from pSUPER-Cdh11-C depicted in FIG. 1(b).

Figure 2:
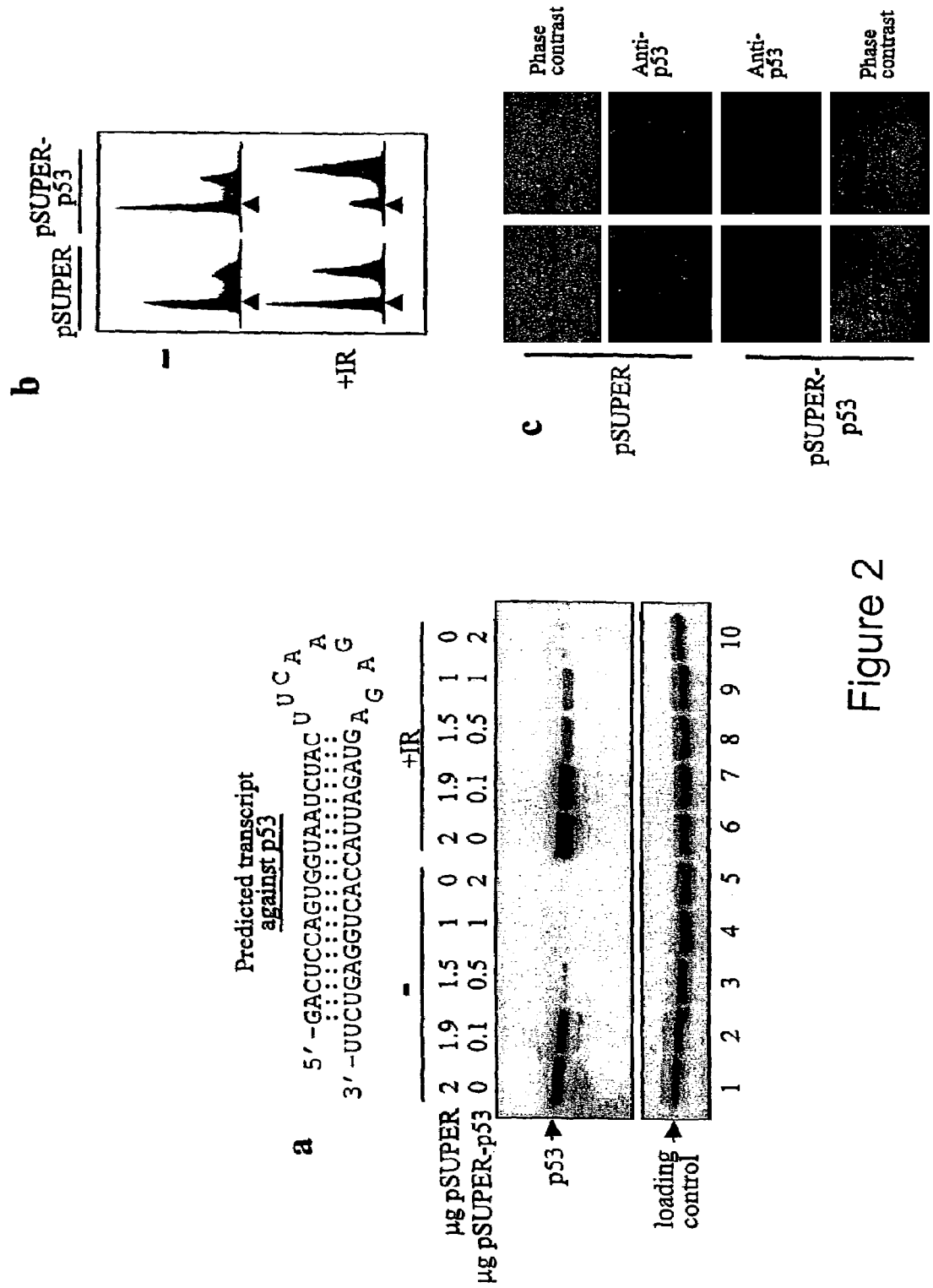
FIG. 2(a) shows a western blot of cells transfected with increasing amounts of the pSUPER-p53 vector, that is predicted to produce the transcript depicted above the blot. Cells were either irradiated (+IR, 20 Gy) or left untreated, harvested, blotted and then probed with anti-p53 antibody as indicated and also probed for a control protein to show equal loading.
FIG. 2(b) shows flow cytometric analysis of cells transfected either with empty pSUPER or with pSUPER expressing the siRNA against p53. The cells have either been irradiated (+IR, 10Gy) or are unirradiated controls (-). Cells with a G1-phase DNA content are indicated with an arrow.
FIG. 2(c) shows cells transfected with 1 µg pSUPER vectors and 0.1 µg pBabe-puro plasmid which were selected with 1 µg/ml puromycin 48 hours later for 12 days. Plates were irradiated (20 Gy) and after 4 hours fixed and stained to detect p53. Shown also are the phase contrast images of the same colonies. The left and right images are of two different colonies.

SEQ ID NO:8 provides the sequence of the predicted stem loop transcript generated from pSUPER-p53 which is also depicted in FIG. 2(a).

SEQ ID NO:9 provides the sequence of the predicted stem loop transcript generated from the pSUPER-Cdh11-B vector as depicted in FIG. 3(a).

SEQ ID NO:10 provides the sequence of the predicted stem loop transcript generated from the pSUPER-Cdh11-B (mut-9) vector as depicted in FIG. 3(a).

SEQ ID NO:11 provides the sequence of the predicted stem loop transcript generated from the pSUPER-Cdh11-B (mut-2) vector as depicted in FIG. 3(a).

Figure 4:
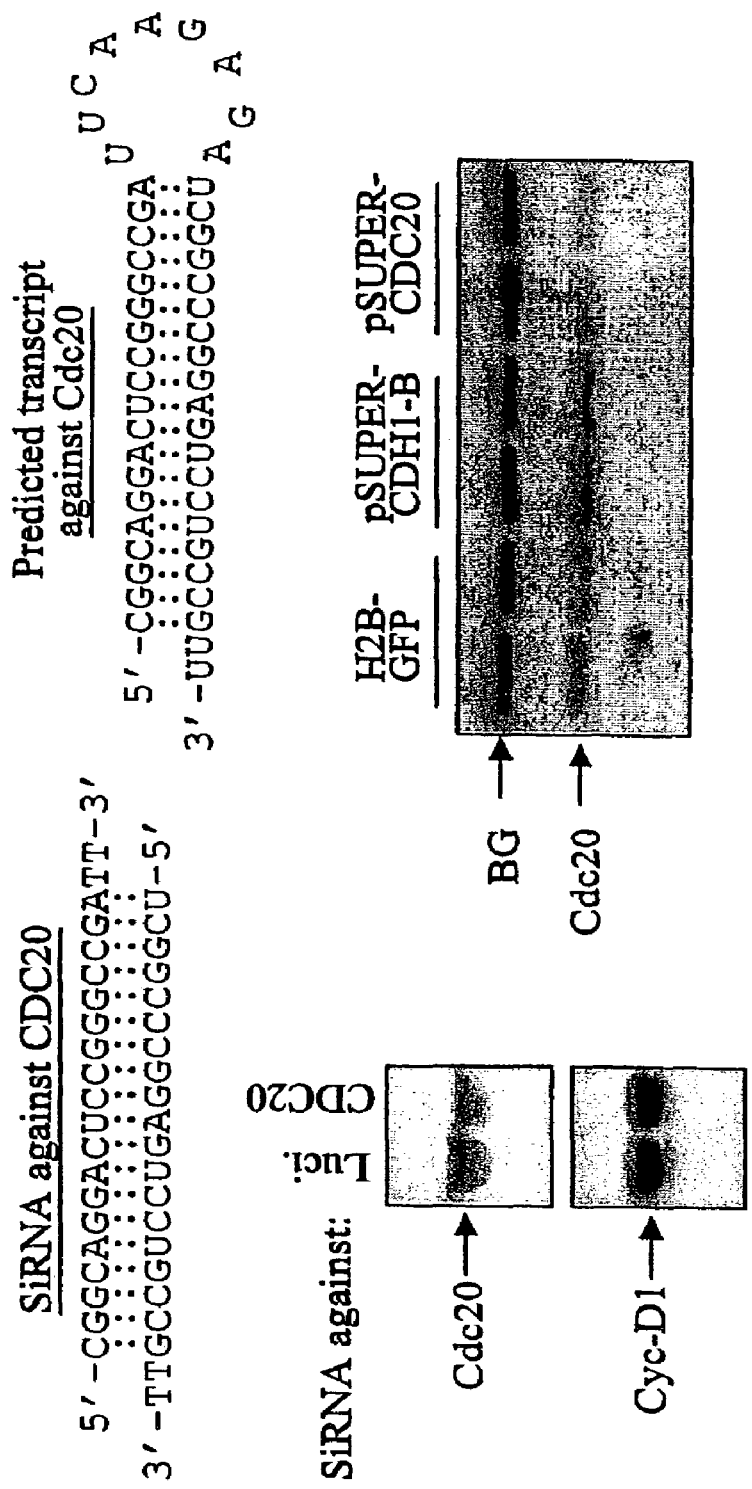
FIG. 4 shows suppression of CDC20 expression by both synthetic SiRNA and pSUPER-CDC20. Shown are the sequences of the SiRNA and the predicted transcript of pSUPER-CDC20 utilized to ihibit CDC20 expression. The indicated SiRNAs and plasmids were transfected into cells, cell extracts immunoblotted and probed to detect Cdc20 and Cyclin D1 proteins.

SEQ ID NO:12 provides the sequence of the sense strand of the synthetic siRNA against CDC20 depicted in FIG. 4.

SEQ ID NO:13 provides the sequence of the antisense strand of the synthetic siRNA against CDC20 depicted in FIG. 4.

SEQ ID NO:14 provides the sequence of the predicted stem loop transcript generated from the pSUPER-CDC20 vector as depicted in FIG. 4.

SEQ ID NO:15 provides the sequence of an oligonucleotide used to generate pS-K-RAS$^{V12}$.

SEQ ID NO:16 provides the sequence of an oligonucleotide used to generate pS-K-RAS$^{V12}$.

Figure 8:
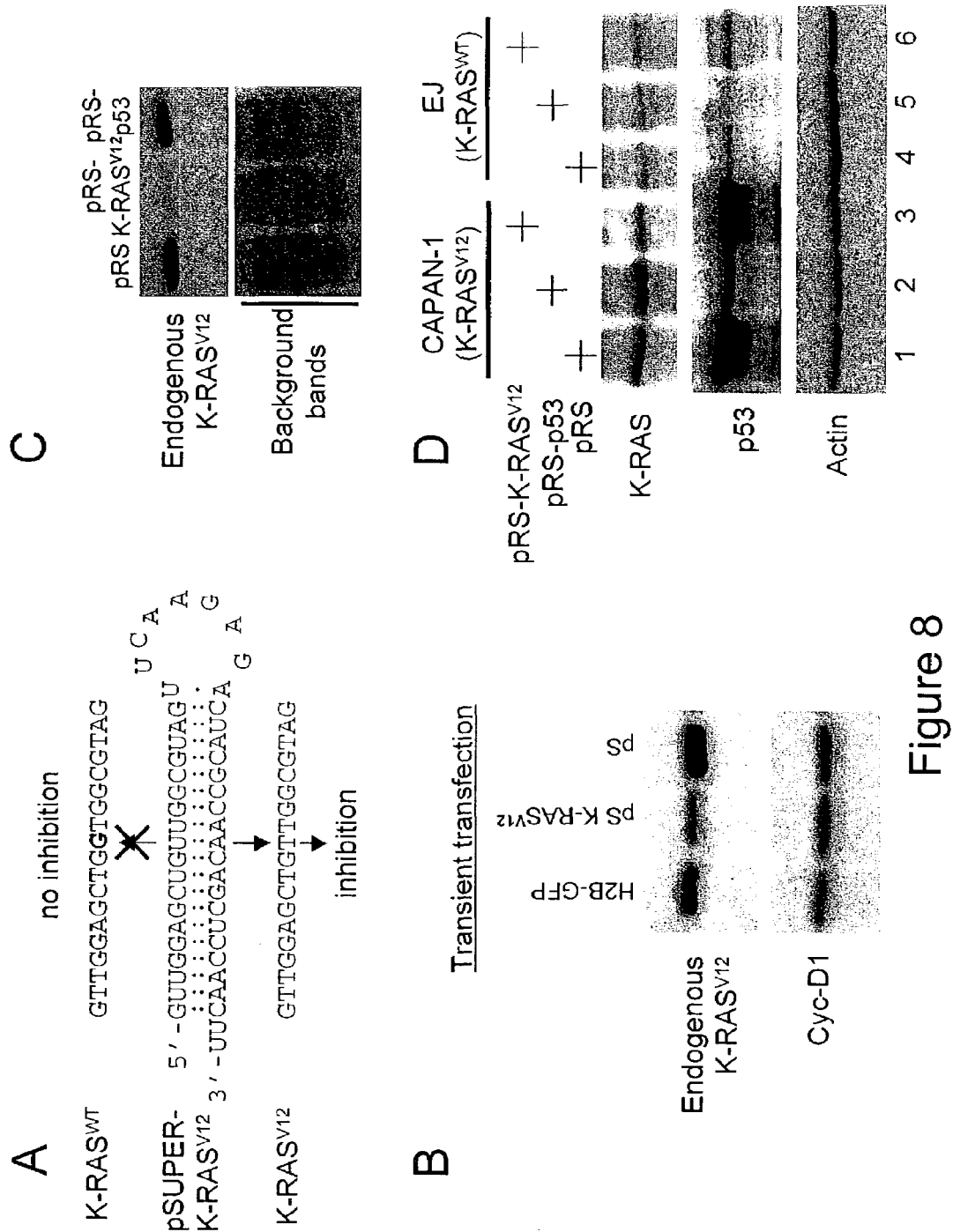
FIG. 8 shows the selective suppression of oncogenic K-RAS$^{V12}$.

SEQ ID NO:17 provides the sequence of a region of wild type K-RAS spanning residue 12 as depicted in FIG. 8A.

SEQ ID NO:18 provides the sequence of a region of mutant K-RAS spanning residue 12 as depicted in FIG. 8A.

SEQ ID NO:19 provides the sequence of the predicted stem loop transcript generated from the pSUPER-K-RAS$^{V12}$ vector as depicted in FIG. 8A.

SEQ ID NO:20 provides the sequence of a preferred spacer region.

SEQ ID NO: 21 provides the sequence of a forward primer used for amplifying a pSUPER cassette.

SEQ ID NO: 22 provides the sequence of a reverse primer used for amplifying a pSUPER cassette.

SEQ ID NO: 23 provides the sequence of an oligonucleotide used to generate pRETRO-SUPER-mp53.

SEQ ID NO: 24 provides the sequence of an oligonucleotide used to generate pRETRO-SUPER-mp53.

Figure 11:
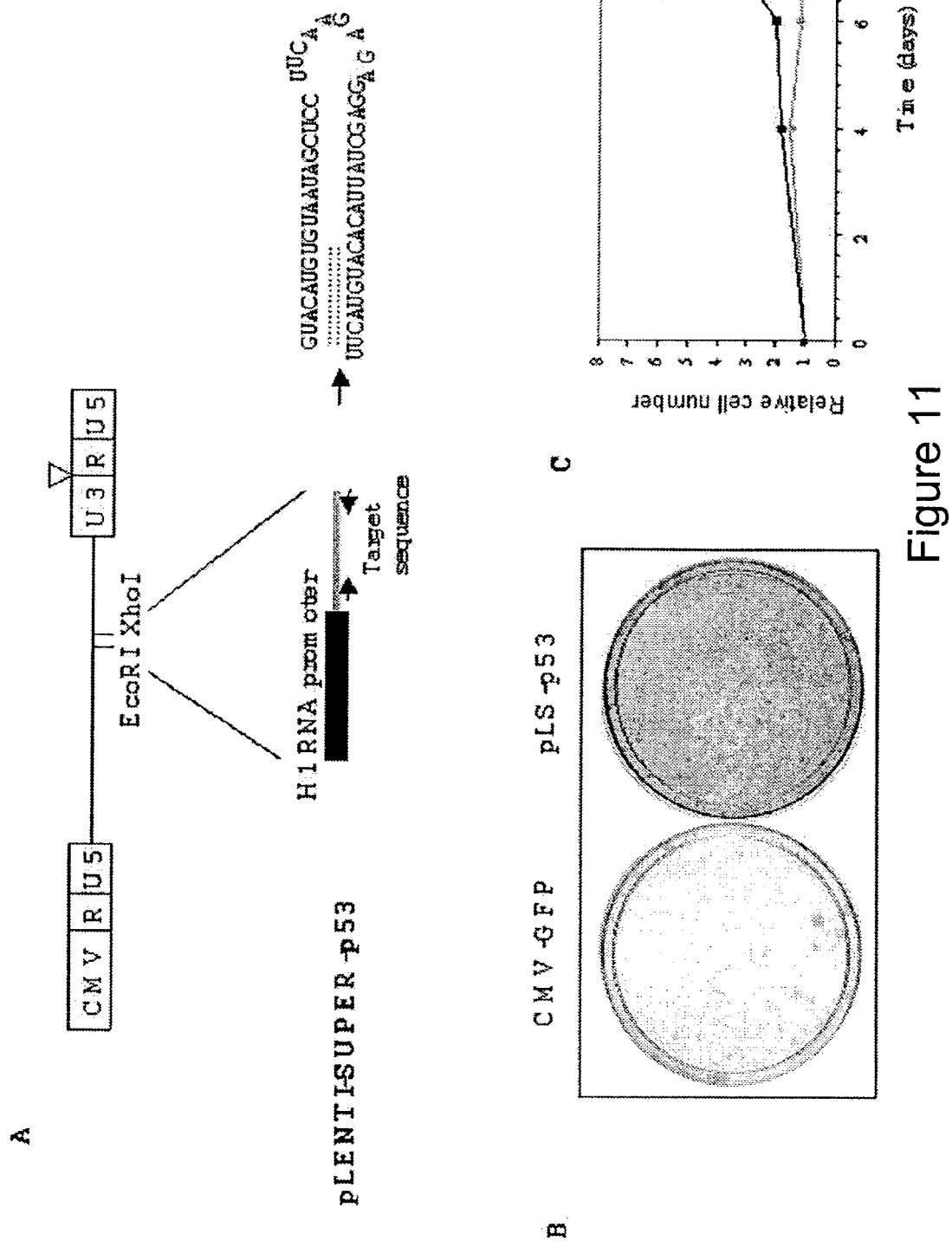
FIG. 11 shows a lentiviral vector that mediates RNA interference. A: A schematic overview of the lentiviral RNA interference vector pLENTI-SUPER-p53 (pLS-p53). A DNA fragment containing the H1 promoter and an oligonucleotide insert targeting murine p53 were transferred from pRETRO-SUPER as described herein to HIV-SC (Miyoshi, et al, (1998). J Virol 72, 8150–8157) by digestion of both vectors with EcoRI and XhoI, followed by ligation of the H1-p53 DNA fragment into HIV-CS. The predicted short hairpin RNA targeting murine p53 is shown. B: Passage 3 FVB wild type MEFs were infected with either HIV-CS-CG (CMV-GFP) lentivirus or LENTI-SUPER-p53 virus, respectively. Forty eight hours after infection $5 \times 10^4$ cells were seeded in 10 cm dishes for colony formation assays and stained after 14 days. C: Forty eight hours after infection $1.5 \times 10^3$ cells were seeded per well in six-well dishes. At varying time intervals cells were fixed and stained with crystal violet, which was then solubilized with 10% acetic acid and quantified at $OD_{590}$ as a relative measure of cell number. CMV-GFP and pLS-p53 curves are marked in gray and black, respectively.

SEQ ID NO:25 provides the sequence of the predicted stem loop transcript generated from the LENTI-SUPER-p53 vector as depicted in FIG. 11A.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows. Where the word "comprising" is used the invention encompasses embodiments which consist essentially of the elements specified.

The present invention provides various polynucleotides, vectors and constructs capable of producing siRNAs. By construct it is meant either a polynucleotide or vector of the invention. The polynucleotides of the invention comprises:
    a RNA polymerase III promoter;
    a region encoding a siRNA; and
    a transcriptional termination element comprising five consecutive thymidine residues.

RNA Polymerase III Promoters

The expression of the siRNA in the constructs of the invention is driven by a RNA polymerase III promoter. Such promoters are typically capable of producing a high level of expression of a particular gene and often well in excess of the levels achievable with RNA polymerase II promoters. This high level of expression can help ensure that a high level of inhibition of the target gene is achievable.

Typically, the level of inhibition of the target gene is at least 20%, preferably is at least 30%, preferably at least 40%, even more preferably is at least 50%, still more preferably is at least 60% of the normal level of expression of the allele or of the elevated level of expression of the targeted where the target gene is abnormally expressed. The level of inhibition may be in excess of 60%, preferably in excess of 75%, more preferably in excess of 90%, even more preferably in excess of 95% of the normal level of expression of the allele or of the elevated level of expression of the targeted where the target gene is abnormally expressed. The fact that the level of inhibition may be specifically chosen is one advantage over gene targeting and other conventional mutagensis methods, where a gene is rendered completely inactive, without the option for gradations of gene inhibition. Thus for a particular situation any of the levels of inhibition specified herein may be used or a level of inhibition as appropriate.

The particular level of inhibition may be chosen, because of the use the methods of the invention are being put to. For example, in cases where a disease is being modelled that involves reduced expression of a gene, but not total elimination of the expression of that gene the level of inhibition may be chosen to match the reduction seen in the disease condition. Alternatively, in some therapeutic methods, where a specific gene is expressed at an elevated level, it may be desired to return the level of expression of that gene to the normal level expression rather than to completely inhibit expression of that target gene. For target validation and drug screening less than a 100% inhibition may be required such as from 20 to 30%, more preferably from 30 to 40% or still more preferably from 40 to 50%.

In a preferred embodiment of the invention the level of inhibition is, or almost is, 100%, and hence the cell or organism will in effect have the phenotype equivalent to a so called "knock out" of a gene. However, in some embodiments it may be preferred to achieve only partial inhibition so that the phenotype is equivalent to a so called "knock down" of the gene.

The RNA polymerase m (pol III) promoters are responsible for the expression of a variety of genes including H1 RNA gene, 5S, U6, adenovirus VA1, Vault, telomerase RNA, and tRNA genes. There are three major types of pol III promoters: types 1, 2 and 3. In addition to type 1 to 3 promoters, several other pol III promoter elements have been reported including those responsible for the expression of Epstein-Barr-virus-encoded RNAs (EBER), and human 7SL RNA. Any of these RNA polymerase III promoters, or functional derivatives thereof, may be used in the present invention to drive expression of the siRNA, the promoter may typically be a type 3 RNA promoter and in particular most preferably the promoter is a type 3 H1 RNA gene promoter. Preferably the RNA polymerase III promoter responsible for the expression of the H1 RNA may be employed. The H1 RNA is the RNA component of the human RNAse P. Type 3 promoters are preferred as they are "external" promoters in other words they are self contained, in that they do no require specific elements to be present downstream of the transcriptional start site for transcription to occur such as in the case of type 1 or 2 promoters. In an especially preferred embodiment of the invention the promoter employed is an external promoter.

As well as various known RNA polymerase III promoter various functional derivatives of such promoters may be employed and in particular a functional derivative of the H1 RNA gene promoter may be employed. Such derivatives will be capable of being recognised by RNA polymerase III resulting in a transcript being generated. Such functional derivatives may comprise combinations of the various elements known to be important in RNA polymerase III promoters.

The promoter will be operably linked to the region encoding the siRNA. Typically, the sequences encoding the siRNA will be immediately downstream of the transcriptional start site or be separated by a minimal distance such less than twenty base pairs, preferably less than ten base pairs, even more preferably less than five base pairs and still more preferably by two or less base pairs.

Typically the RNA polymerase III promoter employed will comprise three consecutive cytosines i.e. CCC, these will normally be the last three nucleotides of the promoter and transcription will start immediately downstream of this CCC sequence. This is especially the case where the promoter is a H1 RNA gene promoter or a functional derivative thereof.

In addition, to the RNA polymerase III promoter the constructs of the invention may comprise various elements to allow for tissue specific, or temporally (time) specific expression. Methods to achieve such tissue or temporally controlled expression are known in the art and any of these may be employed to achieve such expression. By using such mechanisms this may allow the inhibition of the target gene to occur in a specific cell type or stage of development. This may have applications in both therapy and developmental biology for example, where the aberrant expression or mutated allele is only being expressed in a particular cell type or it is not wished to disrupt expression in other cell types or where a gene is only expressed during a particular stage of embryonic development or maturation of the adult organism. It may also allow for the study of essential embryonic genes in mature adults.

By disrupting or inhibiting genes in a tissue or temporally controlled manner insights into gene function can be gained as well as into the function of specific cell types. In gene knockouts often a phenotype is severe or affects multiple cell types so that it is hard to tell the role of a gene in a given cell type which may be important in developing therapies. As well as in developmental biology such methods may also be important in the study of the immune system as it involves multiple lineages and cell types. It may also be possible to eliminate a specific lineage or cell type by disrupting an essential gene only in that cell type or lineage. Again this may be important in animal models, screening and target validation as well as studying the function of the lineage or cell type eliminated.

Transcriptional Termination

A transcriptional termination element is included in the polynucleotide of the invention. The transcriptional terminator is downstream of the region encoding the siRNA and is preferably immediately downstream of the encoding region or separated by a minimal distance.

Typically the termination element will comprise a series of consecutive thymidines and in particular five consecutive thymidine residues in the sense strand of the vector. The advantage of such a transcriptional terminator is that the transcript initiated by the preferred promoter of the invention is normally cleaved after the second uricil to give rise to a transcript ending with two consecutive uridines. These uridines can form one of the 3' overhangs in the siRNA necessary for optimal activity. The cleavage site and hence the overhang generated may vary depending on the precise nature of the type 3 RNA polymerase promoter used, some will lead to the generation of overhangs of two, three, four or five uridines and the particular system will be chosen to give rise to the overhang of choice, which will typically be two uridine residues.

Region Encoding the siRNA

The polynucleotides of the invention comprise a region encoding a siRNA. By siRNA it is meant a short double stranded RNA molecule which comprises a double stranded region which is identical in sequence to a target gene. The siRNA is capable of silencing or inhibiting the specific target gene.

The inhibitory effect of the siRNA of the invention is mediated by the double stranded region of the molecule. It is the double stranded region which is responsible for the specificity of the inhibition and the mechanism by which the siRNA acts. The formation of a complex with a nuclease and subsequent strand exchange of one of the strands of the siRNA with the target RNA transcript all subsequent cleavage of the transcript all involve a double stranded region.

Typically, the dsRNA region of the siRNA has overhangs at one or preferably both of its 3' termini, these overhangs are preferably only a few nucleotides in length and in particular are one or two nucleotides in length and preferably are two nucleotides in length. Although less preferred, the siRNA may be blunt ended or have single nucleotide 5' overhangs at one or both 5' termini.

In situations where the 3' overhangs are dinucleotides, then the preferred 3' overhangs are derived from the first two nucleotides of the loop, being preferably UU or UG, and from the last two nucleotides in the transcript which are invariably UU. In a particularly preferred embodiment of the invention, one or preferably both of the overhangs are UU.

Typically, the double stranded region which is identical in sequence to the target is generated from a stem looped single stranded precursor. The precursor comprises a region identical to a region of the sense strand of the target gene and a second region which is the complement of the first and hence which corresponds to the antisense strand of the target gene. The two complementary regions are usually separated by a short spacer region such that when the two complementary regions hybridise a stem loop or hairpin structure is formed with the spacer forming the loop.

Typically, the region immediately 3' of the first complementary region comprise two consecutive uridine residues and the loop structure can be cleaved. The cleavage typically occurs 3' to the two uridine residues and just before the region complementary to the first. This results in the generation of a siRNA with a dsRNA region identical to the target and with the dinucleotide 3' overhangs necessary for activity. The two nucleotides which give rise to the 3' overhang may be any of the preferred dinucleotides mentioned above. Typically, the cleavage is carried out by an endogenous enzyme and in particular by a homolog of dicer. Alternatively, the construct may also encode such an enzyme.

Typically, the region of sequence identity to the target gene is from eighteen to thirty nucleotides in length, preferably from nineteen to twenty-three nucleotides in length, even more preferably is 21 or 22 nucleotides in length, and still more preferably the region is 21 nucleotides in length. Preferably the region of sequence identity does not exceed 30 bases. The loop of the stem structure may be any size above 6 nucleotides. Typically, the loop may be from 6 to 100 nucleotides in length, preferably it is from 7 to 50 nucleotides in length, more preferably is from 9 to 20 nucleotides in length. In an especially preferred embodiment of the invention the loop is 9 nucleotides in length. The loop, and hence the region encoding, may include various elements such as a regulatory elements which influence transcription or elements which influence RNA stability.

As the polynucleotide of the invention generates a siRNA from a single RNA precursor with a stem loop structure this is preferable to many methods in the art for generating siRNAs where complementary single stranded RNAs are annealed and then the double stranded siRNA has to be purified from unannealed single stranded RNA to ensure optimal performance. It is also more efficient than the use of plasmids comprising opposing promoters transcribing through the same region to produce sense and antisense transcripts which again have to be annealed.

As the invention uses a polynucleotide molecule to express the siRNA rather than transfecting or microinjecting the siRNA itself, this also ensures longer term expression of the siRNA and hence inhibition of the target gene. In addition, the delivery of a DNA molecule such as polynucleotide to a target cell is considerably easier and less time-consuming than the generation of a siRNA and its introduction to the target cell.

Whilst not being wished to be constrained to a particular mechanism it is believed that the siRNA effectively acts as a guide RNA in a sequence specific RNA degradation process. The siRNA is thought to form a complex with a nuclease followed by exchange of one of the strands in the siRNA by the equivalent strand of the transcript of the endogenous gene to be targeted. This means that one of the strands of the siRNA is released and replaced by the region of sequence identity in the target RNA. The strand exchange is followed by cleavage of the transcript, probably at each end of the duplex region.

The cleavage products which are separate from the duplex region are rapidly degraded as they lack either a stabilising cap or poly (A) tail. This cleavage therefore prevents expression of the targeted transcript, but also regenerates the initial complex of a siRNA and nuclease. This means that the regenerated complex can again inactivate another target transcript and so on. The mechanism of action means there does not necessarily have to be an excess in the initial amount of siRNA to be expressed in comparison to the target transcript.

Preferably the region of the target gene which is also present in the siRNA is an exonic region. Typically the region is towards the 5' end of the targeted transcript. In some embodiments of the invention several siRNAs are expressed targeting different regions of the same gene to help ensure maximal inhibition. The different siRNAs will preferably be expressed as separate transcripts, but may be encoded on the same construct. Constructs are also provided which are capable of inhibiting multiple genes by expressing siRNAs specific for each gene. Alternatively, multiple constructs may be used, each of which expresses one or more siRNA specific for a particular gene.

Embodiments of the invention allowing for the inhibition of multiple genes may be used for inhibiting several genes in the same pathway or redundant family members. This may be important in disease models, target validation, drug discovery and the other applications of the invention. The inhibition of multiple genes may allow multifactorial disorders to be modelled.

Often when one gene is inhibited a second gene is able to compensate for the first either totally or at least to some extent. By inhibiting the compensatory gene or genes as well this can be used to produce cells or organisms totally lacking a particular property or function. For example, all of the kinases capable of phosphorylating a particular substrate or class of substrate may be eliminated or embryonic development can be altered.

In situations where several genes in a pathway are inhibited, this may ensure total elimination of the pathway or allow the pathway to be engineered to produce a particular phenotype such as to produce a particular substance such as a desirable metabolite, in excess. Pathways often have feedback mechanisms controlling them and some of these may be eliminated using the methods of the invention.

In some cases, the same siRNA produced may be able to target several genes. Such siRNAs will typically be specific for a sequence present in two or more genes such as an evolutionary conserved sequence in a gene family. Again, this means that two or more genes capable of functionally compensating for each other may be inhibited, but also that a particular gene class may be inhibited. In some embodiments, the siRNA produced may chosen to be able to inhibit homologous genes in different species because of sequence identity or homology between the genes in the two species. Such embodiments may, for example, be useful where the siRNA inhibits a gene of a pathogen such as a viral gene and is capable of inhibiting that gene in several species or strains of viruses because of sequence conservation.

In some embodiments it may be desired to inhibit two or more transgenes, for example in a tissue specific manner, so that they are only active when chosen. In such embodiments, the transgenes may be tagged with a specific sequence present in all of them allowing for them all to be inhibited with a single siRNA.

In some embodiments of the invention, such as to ensure a particular secondary structure in the transcript or siRNA, it may be that the construct or transcript does not have any dinucleotide, trinucleotide, tetranucleotide, or hexanucleotide repeats with more than a certain number of repeats of the dinucleotide, trinucleotide, tetranucleotide or hexanucleotide, such as having less than five, preferably less than ten, more preferably less than fifteen, even more preferably less than twenty such repeats, still more preferably less than twenty five repeats of the dinucleotide, trinucleotide, tetranucleotide or hexnucleotide. In some embodiments of the invention, the limitation on the number of repeats may apply specifically to the number of repeats in the loop of the stem loop and any of the limits mentioned above may apply specifically to the loop although the limitation may also be on the number of repeats in the stem or alternatively on any regions outside the hairpin such as at single stranded regions outside the stem loop. It may also be desired in some cases that these limitations apply to a specific dinucleotide such as GC or a specific tetranucleotide such as AGCT or a specific hexanucleotide such as GAATTC.

Polynucleotides & Vectors

The polynucleotides of the invention may be provided as simple polynucleotides or alternatively in the form of vectors. Preferably, they are provided in the form of vectors such as a plasmid. Such vectors may be shuttle vectors such that they are capable of being reproduced in large amounts in prokaryotic or eukaryotic bacterial systems and then introduced into the target cells.

Many suitable vectors are known in the art. These include without limitation plasmid vectors, such as pBSK, pBR322, pUC vectors, vectors that contain markers that can be selected in mammalian cells, such as pCDNA3.1, episomally replicating vectors, such as the pREP series of vectors, retroviral vectors, such as the pBABE vector series, adenovirus-associated vectors or adenoviral vectors. In particular, the preferred vector is pBSK (Bluescript).

Such vectors may include various selection markers and/or reporter genes. These may be used for selection in the bacterial system the plasmid are grown in, but also for selection of transfected and in particular stably transfected cell lines. Examples of reporter genes which may be employed to identify transfected cell lines include alkaline phosphatase (AP), beta galactosidase (LacZ), beta glucoronidase (GUS), chloramphenicol acetyltransferase (CAT), green fluorescent protein (GFP), horseradish peroxidase (HRP), and luciferase (Luc). Possible antibiotic selectable markers include those that confer resistance to ampicillin, bleomycin, chloramphenicol, gentamycin, hygromycin, kanamycin, lincomycin, methotrexate, phosphinothricin, puromycin, and tetracyclin. The construct of the invention transcribed to generate the siRNA may be double or single stranded nucleic acid, especially preferred is the situation where the construct is double stranded.

The vector of the invention may be one which is capable of integrating into the genome of the cell. Possible viruses which may typically be used to integrate the constructs include retroviral vectors, such as the pBABE vectors, lentiviral vectors, Adeno-associated virus (AAV) vectors. However, most plasmids can integrate at some frequency and hence may be used to generate integrants. Alternatively the vector may be one which is capable of replicating as an extrachromosomal element such as an artificial chromosome or an Epstein Barr based virus.

The vector used to introduce the polynucleotide of the invention into target cells may be a viral vector such as an adenoviral vector, retroviral viral vector, reovirus vector or lentivirus vector. Retroviral vectors are particularly useful for embodiments where it is desired to integrate the vector into the host genome. Various viral vectors, and in particular retroviral and adenoviral vectors are known in the art and any of these may be employed.

The constructs of the invention may be introduced into the target cell or organism using a variety of methods. Where the polynucleotide is introduced into a cell in vitro conventional techniques such as by transfection, liposomes or viruses may be employed. Typically electroporation may be employed. Electroporation may also be used to introduce the constructs into embryos.

In the case of organisms any conventional method of introducing nucleic acids may be employed. A viral construct packaged into a viral particle may be employed. For example viruses such as adeno associated virus, lentivirus, reovirus or a retrovirus may be used. Lipid-mediated carrier transport such as liposomes may be used. Physical means such as bombardment with particles comprising the nucleic acid may be used. The method of delivery may mean that the construct is delivered to a particular location such as an organ or a diseased or inflamed sited. In some situations, the construct will be delivered into the blood, lymph, or cerobrospinal fluid.

The polynucleotides of the invention also includes transcripts and derivatives generated by transcription of the constructs of the invention. In particular, the molecules will comprise the stem loop structure prior to cleavage. The transcript will include the double stranded region responsible for the specificity of the resulting siRNA. Preferably, this region will be specific for a human or viral gene, more preferably the region will be specific for a target gene present in the genome of the target cell, even more preferably the target gene will be an endogenous gene present in the host cell genome, but may be a transgene or viral gene integrated into the host genome. Therefore the target gene of the siRNA molecule will be present in a host chromosome, but may be on an episome or even a plasmid or extrachromosomal element or a viral genome. The transcripts and derivatives may have any of the characteristics or properties specified herein such as size of stem loop, or overhangs etc. Although not a preferred embodiment of the invention, also envisaged are situations where the constructs of the invention are used to generate siRNAs in one system, such as any of the cells mentioned herein, and then transferred into another system to inhibit or modulate a target system.

Target Genes

The target gene may be any gene of which it is desired to inhibit or modulate the function of. The purpose of the inhibition may be therapeutic or to study the function of a particular gene. The inhibition of the gene may be to alter the phenotype of a cell or organism in some desired way such as to improve the characteristics of a commercially reared animal. Typically, the target gene will be a eukaryotic gene, but alternatively the target gene may be prokaryotic such as a viral gene being expressed in a eukaryotic host cell. The target gene may encode a polypeptide or alternatively a structural or enzymatic RNA. However, preferably the target gene encodes a polypeptide.

The target gene may be a developmentally important gene, it may encode a cytokine, lymphokine, a growth or differentiation factor, a neurotransmitter, an oncogene, a tumour suppressor gene, a membrane channel or component thereof, The gene may encode a receptor and in particular one for the gene products of any of the genes mentioned herein. The target gene may be one involved in apoptosis. Typically, the target gene will be one associated with a disease or disorder and the methods of the invention may be used to treat, prevent, or ameliorate that disease or disorder.

The system may be used to treat, prevent or ameliorate cancers. For example, the target gene may be an oncogene, tumour suppressor gene, or gene involved in the control of the cell cycle. Cancers which may be treated include solid tumors and leukemias (for example B cell, mixed cell, null cell, T cell, T-cell chronic, HTLV-II-associated, lymphocytic acute, lymphocytic chronic, mast cell, and myeloid leukemias, melanoma, fibrosarcoma, osteosarcoma, neuroblastoma, neurofibroma, sarcoma (for example Ewing, experimental, Kaposi, and mast cell sarcomas). The cancer may be one of the bone, breast, digestive system, colorectal, liver, pancreatic, pituitary, testicular, central nervous system, lung, urogenital system or prostate. The tumour may be benign or malignant, typically it will be malignant. The tumour may be a primary or secondary tumour and may be metastatic. The medicaments of the invention may be administered on their own or in combination with other anti-cancer treatments such as in conjunction with chemotherapy or radiotherapy. The target gene may be one of a pathogen or host gene responsible for entry of the pathogen into its host, its subsequent replication or other functions such as integration of the pathogen's genome into the hosts, establishment or spread of an infection in the host, or assembly of the next generation of pathogen. The inhibition of the gene may be used prophylactically (i.e., prevention) or to decrease risk of infection, as well as to reduce the frequency or severity of symptoms associated with infection.

In some situations disorders are caused by the elevated or inappropriate expression of a particular gene. For example in inflammatory disorders or autoimmune disorders inappropriate expression of a particular gene may play a part in the pathogenesis of the disorder. In conditions such as arthritis, emphysema, adult respiratory distress syndrome and the like expression of inflammatory mediators, receptors for such mediators, adhesion molecules, and bactericidal activities such as proteases or the respiratory burst may play an important part in the tissue damage occurring. By employing the methods and constructs of the present invention to inhibit genes such as these, and in particular at the particular site of inflammation, these conditions may be prevented, treated or ameliorated. In such embodiments, methods which allow the inhibition to be confined to a particular cell type are particularly preferred.

The target gene may be present in a host cell chromosome or may alternatively be an episomal element or present associated with a pathogenic structure present in the cell such as a viral protein. The target gene may be an endogenous gene or a transgene. Typically, the target gene is a mammalian gene or alternatively a viral gene. In embodiments where the target gene is a viral gene it may be integrated into the host chromosome or present as a non integrated element. The target gene may be a gene on a viral construct or some other vector introduced into a cell.

In many embodiments the target gene is not a reporter gene or a selectable marker although such target genes are also envisioned as possible target genes. Examples of such reporter and selectable markers include any of those mentioned herein and in particular beta galactosidase (LacZ), beta glucoronidase (GUS), chloramphenicol acetyltransferase (CAT), green fluorescent protein (GFP), horseradish peroxidase (HRP), or luciferase (Luc).

Allele Specific Inhibition

The polynucleotides of the invention may be used to inhibit expression of a specific allele, whilst allowing normal expression of the other allele. In such embodiments the two alleles of the gene will have some difference in sequence which will allow them to be discriminated between by the siRNA.

Many disorders result from the mutation of one allele whilst the other allele is normal. These include autosomal dominant conditions as well as some cancers such as where mutation of one of the two copies of a proto-oncogene results in the generation of an oncogene and hence cancer or puts the individual one step closer to developing cancer. By specifically blocking expression of the mutated allele this may allow treatment of the disorder as the remaining wild type allele in the cell may be able to render the cell normal or at least regress the cancer, or ameliorate the condition.

In such embodiments the region of the polynucleotide of the invention identical to the target sequence will be identical to the target allele, but different in sequence to the other allele. Thus, for example, the polynucleotide may include a nucleotide substitution, deletion, insertion or duplication which allows the siRNA generated to discriminate between the two alleles. The siRNA may target an allele generated by chromosomal translocation such as in the case of Burkitt's Lymphoma or Philadelphia chromosome but neither of the wild type alleles of the genes involved in the fusion.

Typically, the sequence difference will be the mutation responsible for the disorder in question. The mutation may be one which is responsible for converting a proto oncogene into an oncogene. For example the mutation may be one in an oncogene such as ras, jun, myc, src, sis, fos, bcl-1 or 2, or abl. However, in some cases the sequence difference may not be the mutation responsible for the disorder, but instead may be a polymorphism allowing the two alleles to be discriminated between. This may mean that the specific mutation associated with the disease may not have to be identified in each individual to be treated as a polymorphism may be more convenient to genotype for. In some conditions, such as those associated with the expansion of a trinucleotide repeat, it may be difficult to generate a siRNA capable of specifically recognising the mutation as the only difference is a duplication or expansion of a repeat in one allele. It may be easier to generate a siRNA specific for a polymorphism within the gene rather than the mutation in question.

Typically, in the siRNA the sequence variation which allows discrimination between two alleles might be located at or near the centre of the double stranded region, such as from five to ten bases into the double stranded region, preferably from seven to ten bases and even more preferably will be nine or ten nucleotides into the duplexed region. In situations where the mutation is not at the centre of the duplex region, it will preferably be located between the 3' end and the middle of the antisense strand of the siRNA. In some embodiments the mutation be close to the end of the double stranded region such as two, three or four nucleotides away.

In some situations allele specific siRNAs of the invention may be used where it is desired to inhibit both endogenous alleles of a gene whilst allowing expression of a transgenic allele. For example, in many cases where a knockout is generated transgenic alleles of the mutated gene are introduced to determine whether the transgene can rescue the phenotype associated with the knock out. This can allow functional analysis of a gene. Therefore, a polynucleotide of the invention may be employed which generates a siRNA capable of inhibiting the expression of both copies of a gene but not of a transgenic allele. The discrimination may be on the basis of a specific polymorphism introduced into the transgenic allele. Preferably, such a polymorphism does not involve an amino acid change or only results in a conservative amino acid substitution. Such methods may also be employed in therapies where it is desired to inhibit the expression of both alleles of a target gene and then express a particular transgenic allele. In some situations, where it is desired to inhibit both copies of an endogenous gene, the two alleles will each have a specific mutation or polymorphism so that a separate siRNA can be employed to inhibit each allele.

The system of the invention may be used to selectively inhibit the expression of particular splice variants. For example, the polynucleotide of the invention may produce a siRNA which targets a particular splice variant which contains an exon it has sequence identity to, but leave intact splice variants lacking that exon.

Target Cells & Organisms

The system of the invention may be employed to inhibit gene expression in a variety of cells and organisms. The system may also be used to inhibit the expression or viral genes in their host cells. Typically, the system is used to inhibit expression in eukaryotic cells and organisms and in particular in mammalian cells or organisms.

The target cell or organism may any organism in which an RNA polymerase III promoter is capable of being expressed in. The organism will usually be eukaryotic, and may be inverterbrate or verterbrate, but is preferably a verterbrate. Preferably, the target cell or organism is mammalian in origin such as of rat, mouse, cow, pig, sheep, or primate origin. In a particularly preferred embodiment of the invention the cell or organism is human. The target may be a virus and in particular a virus when it is present in a host cell.

The cell in which the polynucleotide or vector of the invention may be introduced into or the target gene is expressed in may be from the germ line or somatic cells, totipotent or pluripotent, dividing or non-dividing, immortalized or transformed. The cell may be a multipotent cell or a differentiated cell. Preferred cells include stem cells such as haematopoietic stem cells. Differentiated cell types which may be targeted include without limitation adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, natural killer cells, dendritic cells, keratinocytes, chondrocytes, osteoblasts, osteoclasts, hepatocytes, and cells of the endocrine or exocrine glands. The cells may be those of an established cell or freshly isolated cells. The target cells may be transformed, in particular they may be cancerous and especially malignant cells or cell lines. The cancer may be any of those mentioned herein. Alternatively the target cells may be those infected with a particular pathogen. The target gene may be specifically inhibited in the target cell as opposed to other lineages.

The nucleotide or vector may be delivered ex vivo with the target cell being recovered from the subject, the polynucleotide introduced, and the cells then returned to the subject. Optionally, various selection stages or assessments may be carried out to select and identify clones or cells where the vector has integrated and the target gene is inhibited. Alternatively, the polynucleotide may be introduced into multipotent cells, the cells differentiated into the desired cell type and then introduced into the subject to be treated. Again, optional stages of selection and characterisation may be carried out. Such embodiments are especially preferred for disorders and situations where it is not necessary to inhibit the target gene in all of the particular cells type, and inhibiting expression in a proportion will suffice. Such embodiments may also be used in target validation and drug identification.

In some situations it may be desired to introduce the vector into a multipotent cell and then differentiate it into a number of different cell types to allow screening in several different cell types. In embodiments where the construct is a multipotent cell this may also be used to study the differentiation and differentiation potential of that cell when the target gene is inhibited. This may elucidation of whether a gene plays a role in the differentiation process and if so what role it plays. It may also be used to identify agents or treatments which are capable of influencing the differentiation in a preferable way when the target gene is inhibited.

The polynucleotides or constructs of the invention may be introduced into the target cell or organism via a variety of mechanisms. Where the polynucleotide is introduced into a cell in vitro conventional techniques such as by transfection, liposomes or viruses may be employed. Typically electroporation may be employed.

In the case of organisms any conventional method of introducing nucleic acids may be employed. A viral construct packaged into a viral particle may be employed. For example viruses such as adeno associated virus or a retrovirus may be used. Lipid-mediated carrier transport such as liposomes may be used. Physical means such as bombardment with particles comprising the nucleic acid may be used. The polynucleotide may be introduced into the vascular or extravascular circulation, the blood or lymph system, or the cerebrospinal fluid.

Measurement of Gene Inhibition

In many embodiments of the invention it will be desired to check the efficacy of the siRNAs in blocking the expression of the target gene. The inhibition of the gene may be measured in a variety ways, typically at the RNA, protein or phenotypic level.

Inhibition may be confirmed using biochemical techniques such as Northern blotting, nuclease protection, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

Where the target gene is a mutated allele and the object of the inhibition is to specifically inhibit the mutated allele whilst allowing normal expression of the wild type allele methods may be used to assess inhibition which can discriminate between expression of the wild type allele and the mutated allele such as by single stranded conformational polymorphism, denaturing gel electrophoresis, allele specific PCR or antibodies capable of discriminating between the wild type and mutated proteins.

Inhibition in a cell line or whole organism, may be measured by using a reporter or drug resistance gene whose protein product is easily assayed. Such reporter genes and selection markers include any of those mentioned herein. Inhibition may also be measured at the phenotypic level. For example, the appearance of a phenotype similar to that associated with disruption of the targeted gene may be looked for. Where the purpose of the siRNA is to block expression of a gene associated with a disease whether or not the disease is prevented, ameliorated or treatable using the siRNA may be measured. Where the purpose of the siRNA is to treat an infectious disease any reduction in viral or bacterial load may be assessed or alternatively the presence, absence or severity of symptoms associated with the disorder may be measured.

Integration

In a preferred embodiment of the invention the polynucleotide or vector of the invention is integrated into the genome of the target cell. This helps ensure that the expression of the siRNA is permanent rather than the transient expression associated with non-integrating vectors.

Typically, the polynucleotide or vector of the invention will be integrated into a chromosome of the host cell, although alternatively it may introduced in the form of an artificial chromosome such as a human artificial chromosome or some other episomal element capable of self replication and maintenance in the host cell. Preferably, however the vector or polynucleotide is integrated into a host chromosome.

Particular vectors are known in the art which integrate into the genome of a cell more frequently. For example, the vector used to introduce the polynucleotide of the invention may be a retrovirus or retrovirus based vector capable of integrating into the host genome. Preferred vectors for such embodiments include retroviral vectors, such as the pBABE vectors, lentiviral vectors, Adeno-associated virus (AAV) vectors, retroviral, lentiviral, adeno-associated and adenoviral vectors. Plasmid vectors such as pcDNA 3.1 integrate as well, albeit at lower frequency.

Although episomal vectors may not integrate into the genome at a high level integrants may still be obtained as a low level of integration normally occurs when such vectors are employed. Almost all vectors will integrate into host chromosomes at some level, even if they do so infrequently, as such integrants can probably be generated for any vector. Various methods are known in the art for promoting integration such as irradiation and such methods may be employed.

Preferably, the polynucleotide is integrated into the host genome by random integration. Alternatively, the vector or polynucleotide may be targeted to a specific location in the host cell by methods known in the art such as a site specific recombinase or integrase to integrate the polynucleotide into a specific site. This may allow the vector to be targeted into a known region with particular characteristics such as being permissive for expression or to avoid integration in a gene of the host cell.

After introduction of the target cell of the polynucleotide into the target cell various selection and/or screening techniques may be employed to identify clones in which the vector has integrated and to further characterise them. By employing a selectable marker this may allow selection of the clones in which the vector has integrated such as by looking for expression of a reporter gene such as green flourescent protein (GFP) or by antibiotic selection such as with G418. FACS sorting may be employed to collect cells expressing a particular marker gene such as GFP.

Typically, after transfection the cells will be grown for a sufficient period of time such that transient expression will not be the reason for drug resistance or reporter gene expression. For example, the cells may be grown for more than a week, preferably for ten days and more preferably for two weeks before selection and characterisation.

The vector or polynucleotide may also include means by which the selectable marker or reporter gene can be removed leaving the region capable of expressing the siRNA present in the cell. For example, the selectable marker may be flanked by recognition sites for a site specific recombinase. The selected clone may be transiently transfection with a plasmid capable of expressing the recombinase and then the transfected cells plated and clones from which the selectable marker has been excised selected or identified.

Clones which have integrated the vector or polynucleotide of the invention may be further characterised. For example, Southern blotting or PCR may be carried out to check the plasmid has integrated, determine the site of integration and copy number of the integrated plasmid. The site of integration may be characterised to ensure that it is not an endogenous gene or other important element. Northern blotting or other such techniques may be carried out to determine whether the siRNA is being expressed and to check whether the target gene is being inhibited. Any of the techniques mentioned herein for measuring the inhibition of the target gene may be employed and checks may be made to ensure that the inhibition is specific.

Transgenic Organisms

The polynucleotides of the invention may be used to generate non-human transgenic organisms in which the expression of a target gene is inhibited or reduced. The transgenic animals will preferably have a polynucleotide or vector of the invention integrated into its genome and hence can transmit the integrated polynucleotide or vector to its progeny. However, the invention also encompasses normal animals into which cells comprising the polynucleotide or vector of the invention are transplanted or transferred into. Such animals may provide a model for a particular therapies involving ex vivo treatments.

The transgenic animals may be generated by any of the techniques known in the art for introducing transgenes into animal and in particular by pronuclear injection where the vector or polynucleotide is microinjected into the pronucleus of an oocyte. Transgenic organisms can also be generated by introducing nucleic acid constructs into early embryos such as by electroporation and such methods may be employed to generate the transgenic organisms of the invention. The non-human transgenic animal may be a transgenic rodent, such as a mouse or rat, a primate, or a commercially important animal such as a sheep, cow, or pig. Preferably the organism is a mouse or rat.

The transgenic organisms of the invention may be used as animal models. Alternatively, the transgenic organism may be a commercially raised animal and the introduction of a polynucleotide or vector of the invention means the transgenic organism has a desirable phenotype such as disease or pathogen resistance.

In addition, to comprising a polynucleotide or vector of the invention the transgenic animal may also comprise additional transgenes. For example, the transgenic animal may comprise a modified allele of the target gene and the siRNA be specific for the endogenous alleles of the gene. This may allow an animal model to be developed to assess the functionality of the modified allele introduced as a transgene.

Disease Models

The methods of the invention allow the generation of models of various disease conditions and disorders. For example, they may be used to generate a cell line or an organism in which a specific gene is inhibited. They may also be used to generate models in which both copies of a chosen endogenous gene are inhibited and a mutated allele of the endogenous gene is expressed so modeling conditions such as an autosomal dominant condition or cancer.

Models produced using the methods of the invention may be used to assess the therapeutic efficacy of test agents. The prevention, relief or amelioration of the conditions or symptoms associated with a disorder may be measured. The model may be an a model of an infectious disease such as viral infection and the assay may be used to assess whether infection can be prevented, the load of the pathogen can be reduced, viral integration can be prevented or other symptoms can be treated or ameliorated.

The model may be of the entire disease condition or may be of part of, or a stage in, the condition such as, a step involved in the underlying pathogenesis of the disorder. The model may be of a particular cellular function thought important in the disorder such as, for example, migration, chemotaxis, apoptosis, degranulation, adhesion, phagocytosis or any of the cellular functions mentioned herein.

A large number of genes have been implicated in, or are known to cause, specific disorders and by modulating the expression of these genes using the methods of the invention the same disorders can be modeled in cells or organisms. Various knockout and classically generated mutant models exist and equivalent models may be generated by inhibiting the expression of the gene in question. This may be particularly useful where the existing model is only available for one species, strain or cell and it is desired to rapidly generate a model in a different species, strain or cell line by inhibiting the same gene or its homolog. The methods of the invention may also allow multiple genes to be disrupted in the same organism without having to undergo laborious and lengthy breeding programs. This means that multifactorial disorders can be simply and rapidly modeled.

One of the preferred uses of the model systems of the invention is in screening and target validation. Thus the model may, for example, be used to screen agents to identify those agents which may be useful in treating or preventing the condition being modeled. Promising agents from initial screens may be assessed and characterised further, such as by studying them in more detail in the same or other model systems of the invention. For example, the initial screen may be cell based and may then be followed by characterisation of promising candidate agents from the initial screen in a transgenic organism of the invention.

As in the case of conventional knockouts, using the model systems of the invention means that therapies can be tested and evaluated before they are applied to the actual disease sufferers and also provide the possibility of high throughput screening so that a varying large number of candidate agents can be screened to identify promising candidates for therapeutic use and further assessment. The model systems of the invention, and in particular the transgenic organisms, may also be used to develop, improve or assess methodology in treating conditions such as improved surgical methods.

The model system may be cell based and the particular cell type important in the condition or affected in the condition may typically be used. For example, immune cells may be used in models of inflammatory disorders or for cancers the particular cell type involved in the type of cancer may be used. Alternatively, other cell types known to be suitable for the particular assay methods being employed may be used, rather than those cell types affected in the specific disorder being modeled. Any of the cell types mentioned herein may be used in disease modeling. The cell type may be a multipotent cell and be differentiated into different types of cell to allow screening, target validation and the other applications of the invention to be carried out on multiple lineages including cells in the process of differentiation. The model system may involve multiple different cell types. The interactions of the cell types may, for example, be monitored.

The cells may be assessed in a variety of ways such as at the biochemical, molecular level or functional level. This is discussed further below. The cells may be treated with various agents, or be exposed to specific conditions, which facilitate the modeling of the disease condition. In essence, any of the factors involved in a disorder such as those thought to be important in triggering its onset or involved in its subsequent development may be administered. Such agents may also be used in the animal models of the invention. The substance may be, for example, the actual substance involved in the condition or another substance capable of having an equivalent effect. For example, the cells may be exposed to agents that cause apoptosis, cell death, cell activation, degranulation, transformation or other cellular functions such as any of those mentioned herein. The cells may be exposed to a particular allergens, immunogenic substances, or inflammatory mediators such as those involved in a disorder.

The model system may be a non-human transgenic animal of the invention. Alternatively, cells of the invention may be introduced into normal animals or mutant animals. In many conditions, a specific cell type or lineage may be implicated in the pathogenesis and these may be introduced into an organism. For example, cells of the immune system are implicated in various inflammatory disorders and immune cells or their progenitors, in which a target gene has been modulated using the method of the invention, may be introduced into an animal. The recipient animal may lack the cell types being transferred into it, for example it may have been irradiated in the case of immune cells or may be an animal suffering from SCID or some other immunodeficiency meaning that it lacks specific cell types. The cells being introduced from the animal may originate from that animal.

The generation of the model may also involve various stages such as physical or chemical insult or surgical methods to replicate or induce the disorder being modeled. For example, spinal injury may be induced or liver damage induced using agents such as, for example, carbon tetrachloride. Immune disorders may be induced by, for example, exposure to specific antigens. In many cases the agents known to lead to a disorder, or ones having an equivalent effect, will be administered to induce or model the desired condition. The models may involve infection with pathogens such as viruses. Such methods apply to both cell based and animal models of the invention.

As well as use in target validation, screening and the development of various treatments the models of the invention may be used to gain an insight into the pathogenesis of disorders and into the genes involved. The models may be studied to determine how the disease develops. They may be used to confirm the role of a candidate gene in a disorder. The models may allow a better understanding of the disease to be gained at the biochemical, molecular, genetic, or cellular levels and hence may allow the rational design of new therapies. Various mutated alleles of the gene involved in the disorder may be tested to see if they can be used to rescue or prevent a disease phenotype to analyse what are the essential regions of a particular portion of a gene and what the function of a particular region of a gene or its protein product is. They may be used to demonstrate that a particular portion of a gene has a given function such as enzymatic activity.

The ability to model a human disease in an animal or a cell means that various tests and assays not possible on samples from human patients can be carried out helping to generate further understanding of, and treatments for, the disorders. This may also help save on the inconvenience for patients of having to repeatedly provide samples and be important in cases where a condition is rare in incidence and hence patient samples are not readily available.

Screening & Target Validation

The invention provides for the use of a cell or animal model of the invention to be used to screen candidate agents and identify those that can prevent, treat or ameliorate the condition in question. The model may also be used in target validation to further characterise candidate agents thought to have potential therapeutic value in a condition or to confirm that a candidate gene is involved in a disorder.

Preferably, the assays will be high throughput assays. Assays which can screen large numbers of test agents may typically be employed such as various multiwell plate based assays. These may involve all, or the majority, of the stages of the invention being carried out in the multi-well plate or may involve individual stages of the assay being carried out in the multiwell plate.

The assay may involve growing or culturing cells of the invention in a multi-well plate, contacting them with a test agent, and then looking for such particular phenotype. In some cases the phenotype may be assessed from observing the cells or by employing an assay systems that uses the same plate. The assay may involve growing cells in one multiwell plate, and then removing culture supernatant or cells to be analysed, typically in another multiwell plate. The assay may involve analysing multiple test samples from animals of the invention in a multiwell plate. Preferably, the screening methods employed may be partially or totally automated. Multiwell plate formats are particularly well suited to automation. Various ways to streamline or screen multiple samples are known in the art and these may be employed.

Stages such as the analysis of phenotype may also be automated or performed by an operative. The results obtained may be analysed by computer. Techniques, employing various labels and colour changes may be employed and are often suitable to automation. The label may, for example be enzymatic, radioactive, or fluorescent. Techniques such as PCR, antibody based assays and ELISA may be used as again these may allow multiple samples to be screened and give the option of automation. Where the change being monitored is at the genetic level, such as expression of a transcript or a protein, various assays such as microarrays, chips and membrane based assays may be used. FACS may also be used.

Test agents may be used in an initial screen of, for example, 10 agents per reaction, and the agents of these batches which show the desired phenotype tested individually. Test agents may, for example, be used at a concentration of from 1 nM to 1000 μM, preferably from 1 μM to 100 μM, more preferably from 1 μM to 10 μM. The activity of a test agent may be compared to the activity shown by a molecule used to treat the condition in question The assay may be such that the desired agent gives rise to the expression of a reporter gene or of a selectable marker. This may also facilitate the screening of large numbers of test agents and make it easier to identify the desired clones. Any of the selectable markers and reported genes mentioned herein may be used in such embodiments.

Suitable test agents which can be tested include combinatorial libraries, defined chemical entities and compounds, peptide and peptide mimetics, oligonucleotides and natural product libraries, such as display (e.g. phage display libraries) and antibody products. Typically, organic molecules will be screened, preferably small organic molecules which have a molecular weight of from 50 to 2500 daltons. Candidate products can be biomolecules including, saccharides, fatty acids, steroids, purines, pyrimidines, derivatives, structural analogs or combinations thereof. Candidate agents are obtained from a wide variety of sources including libraries of synthetic or natural compounds. Known pharmacological agents may be subjected to directed or random chemical modifications, such as acylation, alkylation, esterification, amidification, etc. to produce structural analogs.

The agent may be a polynucleotide (single or double stranded) typically with a length of at least 10 nucleotides, for example at least 15, 20, 30 or more polynucleotides. The agent may be molecule which is structurally related to polynucleotides that comprises units (such as purines or pyrimidines) able to participate in Watson-Crick base pairing. The agent may be a polypeptide, typically with a length of at least 10 amino acids, such as at least 20, 30, 50, 100 or more amino acids.

A number of mutated alleles of the gene being inhibited by the siRNA may be introduced into a cell or animal of the invention and the phenotype of the cell or organism. Alternatively, the introduced nucleic acids may be different genes from that inhibited by the siRNA. Various nucleic acid libraries may be screened to identify a nucleic acid capable of producing the desired phenotype. Various mutagenesis techniques may be used to generate the libraries being screened such as to generate mutants from a given sequence either in a directed or random way. A test gene may be a candidate nucleic acid for gene therapy and various variants assessed to identify the optimal sequences. Various delivery methods for delivering a given nucleic acid to a cell may be assessed. Target validation, gene therapy, and other therapeutic applications may well require the administration of multiple genes or nucleic acids. The expression of multiple genes may be advantageous for the treatment of a variety of conditions and the models can be generated where multiple nucleic acids are delivered.

Knowledge about the condition being modeled in the screen may be used to help select what agents are to be screened. For example, the candidate agents for screening may be chosen by rational design. Rational drug design (RDD) methods accelerate the discovery process for useful pharmaceutical agents. RDD typically involves the design and optimization of small, organic therapeutics from the ideal case, where a protein structure is available. RDD may employ techniques such as molecular graphics and simulation technology. RDD may employ three dimensional searching of large databases to identify small molecule fragments which can interact with specific sites in a target molecule, bridging fragments with the correct size and geometry, or framework structures which can support functional groups at favorable orientations. A three dimensional pharmacophore hypothesis or a quantitative structure-activity model (QSAR) may be developed, that is converted into a search query or a predictive formula to search a three dimensional database for structures that fit the hypothesis within a certain tolerance, or the QSAR model may be used to predict activities on novel compounds. Cluster analysis and two dimensional and three dimensional similarity search techniques to identify potential new leads may be employed.

The ability to monitor the phenotype of a cell or organism of the invention is important in the various screening and target validation methods of the invention. Thus the ability of a test agent to modulate the phenotype of a cell or organism, such as in preventing a specific phenotype from developing, causing it to develop, or causing it to regress to a more normal phenotype, may be monitored to identify desirable agents or methods such as, for example, for therapeutic or diagnostic use.

As used herein the term phenotype refers to the characteristics of a cell or organism resulting from the interaction between its genetic makeup and the environment. The phenotype in question will typically be any manifestation of a specific disorder or infection including any of those mentioned herein. Alternatively, the particular phenotype may be some desirable non-disease associated phenotype which it is wished to obtain, such as an increase in the yield of a desirable product in a particular cell type or organism.

The term phenotype is intended to include characteristics such as ones at the biochemical, molecular, cellular, tissue, organ, developmental, cognitive, or behavioural level. The phenotype being assessed may be one resulting from injury, trauma, or chemical or physical insult. The assessment may be at the genetic level such as to see whether the expression of a particular gene, other than that targeted by the siRNA, is modulated by candidate agents. The activity of a receptor, signal transduction protein, membrane channel or enzyme may be monitored. Particular cellular functions such as, for example, migration, adhesion, degranulation, phagocytosis, apoptosis, differentiation, and chemotaxis may be monitored and any change observed. The transformation of a cell or the acquisition of characteristics associated with a cancer may be monitored as a possible phenotype. For many genes the symptoms and associated phenotype of a particular disorder or infectious disease are known as may be the underlying pathogenesis of the disorder. This means that the particular characteristic being studied may be chosen on the basis of such knowledge. The phenotype may be one associated with any of the diseases, disorders, infections, conditions or states mentioned herein.

The assessment of phenotype may be performed on an animal model. This may be done after an initial screen to identify promising candidate agents in cell based assays or may be the primary screen. The animal model may be one of an infectious disease and characteristics such as viral load, infectivity, prevention, amelioration or treatment of the infection may be measured. Preferably the characteristic being measured will be one of central importance to the disease and one whose prevention may improve the condition of sufferers of the disease.

The sensitivity of an animal model of the invention to developing tumours may be monitored. These may have arisen in the animal or have been transplanted into it The metastasis of tumours from one site to another may be monitored. The early stages, before a tumour is actually malignant or metastatic may be monitored. Developmental disorders and in particular those of the embryo may be monitored. In such cases embryos may be harvested from an animal at various stages of development such as is appropriate. Techniques such as embryo transfer may be used to return the embryos to a pseudopregnant female may be carried out to monitor their subsequent development.

Pain may be monitored using any suitable assay for monitoring the behavioral response of an animal to pain stimuli. Control responses may be determined by testing an animal prior to administration of a candidate agent. Learning or cognitive ability may be assessed using such methods as mazes. Aggression may be monitored. The ability of a model organism to raise and care for its young successfully may be measured.

In the screening and target validation methods of the invention various controls such as cells or animals without inhibition of the target gene, to which no agent has been administered or a placebo has been given. Positive controls may include existing modulators which it is desired to improve on.

Generally a test agent may be considered to influence a phenotype if it inhibits or enhances the phenotype, for example expression of a phenotype may be increased or decreased by at least 5%, for example by at least 10%, at least 15%, at least 20% or at least 25%, preferably by at least 30%, for example at least 40% or at least 50%, more preferably by at least 70%, for example, at least 80% or at least 90% compared to controls. In a preferred embodiment of the invention the test agent will be able to turn an abnormal phenotype into a normal one or prevent the development of an abnormal phenotype. The agent may reduce or eliminate a specific symptom associated with a disease.

The methods of the invention may be used to confirm that a candidate gene is actually involved in a particular condition, phenotype or function. For example, the candidate gene may have been identified on the basis of gene mapping to a particular area containing several genes, due to its homology to a known gene (such as a known disease gene) or using a functional based gene cloning strategy. The gene may have been identified as a candidate as it is one of those whose expression changes in a disorder.

Whether or not the candidate gene is actually involved in the function in question may then be confirmed by inhibiting the gene using the methods of the invention. The phenotype of the cell or organism produced may then be studied such as, for example, by any of the methods described herein or employing assays known in the art for assessing such functions. The characteristic may, for example, be one at the biochemical, molecular, genetic, cellular, or organism level, it may be any of those mentioned herein. In the case of cells the characteristic being studied may typically be at the biochemical, molecular, genetic, or cellular levels.

In the case of organisms the characteristic may be at the biochemical, molecular, genetic, or cellular levels or may be, for example, at the organ or system level. The characteristic may be behavioural or cognitive or it may be a symptom associated with a disease. Whether or not the model generated mirrors the disease in question will typically be studied.

In some cases the candidate gene may not be matched to a particular condition. For example, the candidate gene may have homology to a known disease, but whether it is actually implicated in a disorder, and if so what disorder, may not be known. By using the methods of the invention what function the gene plays and what, if any, disorder it may play a part in may be elucidated. This may the identification of specific genes playing a role in a condition. In some cases the genes may be known, but not have been previously been associated with such a disorder and this may provide new therapeutic targets for that condition.

Libraries

The vectors of the invention can also be used to generate large collections of siRNAs to perform genome-wide screens for genes that act in biologically relevant pathways. Therefore libraries of siRNAs can be generated using the invention. Genetic "loss-of-function phenotype" screens using such libraries may yield novel therapeutic targets that are candidates for drug development or may be used to evaluate the contribution of a limited number of candidate genes to a biological response.

Phenotypic genetic screens using cDNA expression libraries have been very successful for selection of genes that act in a dominant fashion to modulate cell behavior. The siRNA gene libraries allow, for the first time, a genome-wide evaluation for loss-of-function phenotypes in mammalian systems. This means that the equivalent of a homozygote for a recessive mutation may be generated.

Sequences to be inserted in the siRNA vector of the invention can be selected in silico by screening the appropriate databases for unique short nucleotide sequences, of the lengths specified herein for the double stranded region of the siRNA of the invention, such as typically 19mers, for every known gene and every EST or a substantial proportion of these. Collections of unique short nucleotide sequences may be synthesized as part of a longer oligonucleotides, such that it will form the characteristic stem-loop structure described herein, then expressed in the siRNA vector, and will be inserted in the siRNA vector.

Such libraries may be based on human gene sequences for use in human cell systems or of species such any of those mentioned herein and in particular those of mammalian origin, or alternatively pathogenic origin such as viral origin.

Libraries of siRNAs can be introduced into the appropriate cell system and a response of the cells can be monitored. Any of the assays mentioned herein may be used to monitor the cells. The cells that show an altered response can be identified in various ways, depending on the nature of the biological system, and the siRNA that is expressed in the identified cell type can be recovered by several strategies, including PCR-based amplification of the specific siRNA insert using vector-specific primers.

Therapeutics

The various polynucleotides, vectors, cell lines and agents identified using the screening methods of the invention may be used in methods of treatment of the human or animal body by therapy or diagnosis. They may be used to prevent, treat, ameliorate or diagnose specific disease conditions or infections condition.

The disease conditions may be any of those associated with the possible target genes mentioned herein. They may be any condition involving a dominant mutation which is either inherited or which results from a dominant mutation in the somatic or germ line tissue of an organism. They may also be conditions which result from the aberrant or inappropriate expression of a target gene.

The condition may be a cancer, and in particular a malignant cancer and especially one which is metastatic. The cancer may be any of those mentioned herein. The condition may be an inflammatory disorder or an autoimmune disorder. The condition may be a developmental disorder. It may be an inherited autosomal dominant condition. Infectious diseases may also be treated or prevented and in particular viral diseases such as retroviral diseases and especially HIV.

The polynucleotide, vector, cell, or agent of the invention may be formulated with standard pharmaceutically acceptable carriers and/or excipients as is routine in the pharmaceutical art. For example, a suitable agent may be dissolved in physiological saline or water for injections. The exact nature of a formulation ill depend upon several factors including the particular agent of the invention to be administered and the desired route of administration. Suitable types of formulation are fully described in Remington's Pharmaceutical Sciences, Mack Publishing Company, Eastern Pennsylvania, $17^{th}$ Ed. 1985, the disclosure of which is included herein of its entirety by way of reference.

The therapeutic entity may be administered by enteral or parenteral routes such as via oral, buccal, anal, pulmonary, intravenous, intra-arterial, intramuscular, intraperitoneal, topical or other appropriate administration routes.

A therapeutically effective dose of the therapeutic molecule or agent of the invention is administered to a patient. The dose may be determined according to various parameters, especially according to the agent used; the age, weight and condition of the patient to be treated; the route of administration; and the required regimen. A physician will be able to determine the required route of administration and dosage for any particular patient. A typical daily dose is from about 0.1 to 50 mg per kg of body weight, according to the activity of the specific modulator, the age, weight and conditions of the subject to be treated, the type and severity of the degeneration and the frequency and route of administration. Preferably, daily dosage levels are from 5 mg to 2 g.

In the case of the nucleic acids of the invention these may be administered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

EXAMPLES

The following Examples further illustrate the present invention.

Example 1

Introduction of synthetic short interfering RNAs (siRNAs) into mammalian cells can significantly suppress expression of specific genes However, this reduction in gene expression is transient. To overcome this limitation, an expression vector, termed pSUPER was generated which directs the synthesis of siRNA-like transcripts (pSUPER, suppression of endogenous RNA). The pSUPER vector was made by digestion of the pBSKII+ (Bluescript) plasmid with EcoRI and BgLII and ligating to it the PCR product of H1-RNA gene promoter.

The human H1 RNA gene sequence available on the NCBI database, accession number X16612, was used. The H1 RNA gene promoter sequences from nucleotide 146 of the genbank sequence (an Eco RI restriction enzyme cleavage site) up to nucleotide 374 were cloned to generate the pSUPER vector. The last three nucleotides of the H1 RNA gene promoter in the vector are CCC, transcription starts immediately downstream of this CCC sequence in the H1 RNA gene. As such, the CCC sequence is a relevant part of the promoter construct. The termination sequence is a stretch of 5 consecutive T residues and was added by PCR downstream of the promoter in the vector.

A schematic drawing of the basic pSUPER vector is depicted in FIG. 1(a) The H1-RNA promoter is cloned in front of the gene specific targeting sequence (typically 19 nucleotide of sequence from the target transcript separated by a short spacer from the reverse complement of the same sequence) and five thymidines (T5) in the sense strand of the vector as termination signal. The basic pSUPER construct was then modified to express a variety of stem loop structures capable of giving rise to siRNAs.

Three pSUPER constructs, pSUPER-Cdh1 A, B and C were generated which contain a 19 nucleotide region identical in sequence to a portion of the Cdh1 gene. FIG. 1(b) depicts the synthetic SiRNA used to target CDH1 generated from the constructs and the predicted secondary structures of the three pSUPER-CDH1 transcripts from the tree constructs A, B and C. The constructs were then transfected into MCF-7 cells using the protocol described in Agami, & Bernards. Cell 102, 55–66 (2000) which gives a transfection efficiency of more than 90%. 1 µg from the indicated DNA constructs and 1.5 µg of SiRNA were transfected into the cells. Sixty hours later whole cell extracts were prepared, separated on 10% SDS-PAGE and immunoblotted to detect CDH1 protein. An immunoblot with anti-Cyclin D1 antibody was used as a control for protein loading. FIG. 1(c) shows the resulting western blot. From left to right the lanes are loaded with cell extracts from cells transfected with a control plasmid expressing GFP, Cdh1-siRNA, the empty pSUPER construct, the three pSUPER constructs capable of expressing the transcripts A, B and C and finally empty pSUPER.

The results show that the pSUPER-Cdh1B construct capable of expressing transcript B which has a stem loop structure where the loop has is 9 nucleotides in length is capable of eliminating up to 90% of Cdh1 expression and achieves an equivalent level of inhibition to the transfection of the synthetic siRNA itself. The pSUPER-Cdh1A construct, where the resulting transcript has a loop of seven nucleotides result in some inhibition of Cdh1 expression whereas the pSUPER-Cdh1C construct where the loop is five nucleotides is inactive. This emphasises the importance of the size of the loop of the stem loop structure in generating siRNA.

Importantly neither the transfection of the synthetic CDH1 SiRNA, nor introduction of the SiRNA expression vectors, had any detrimental effect on cell survival or cell cycle profile (data not shown).

U2OS cells were also transfected as described above with either the synthetic siRNA, empty pSUPER vector, the pSUPER-Cdh1B construct. Total RNA was extracted 60 hours later. Thirty µg of RNA was loaded on an 11% denaturing polyacrylamide gel, separated and blotted as described in Lee et al., Cell 75, 843–54 (1993) with a $^{32}$P-labeled anti-sense 19 nt Cdh1 target oligonucleotide and visualized by PhophorImager (4 hours exposure). The blots were also probed with a sense strand. The control 5S-RNA band was detected with EtBr staining as a control for RNA loading. The resulting blot is shown in FIG. 1(d). The blot shows that the pSUPER-Cdh1B construct results in the generation of an RNA molecule similar in size to the siRNA molecule itself implying that the hairpin loop is cleave to give rise to siRNA molecules.

Example 2

The ability of the methods of the invention to inhibit p53 was assessed. The tumour suppressor p53 is a transcription factor that is stabilized following ionizing radiation (IR) and plays a crucial role in the maintenance of cell cycle arrest in GI following DNA damage (Agami & Bernard, supra and Pluquet, & Hainaut, Cancer Lett 2001, 174, 1–15).

A pSUPER construct, pSUPER-p53, was generated capable of giving rise to the transcript depicted in FIG. 2(a) was generated. Again the vector include a 19 nucleotide region of sequence identity to a region of the p53 gene and a complement of that region.

MCF-7 cells were transfected with increasing amounts pSUPER-p53. Sixty hours after transfection cells were either irradiated (+IR, 20 Gy) or left untreated, harvested 2 hours later and separated on 10% SDS-PAGE. Immunoblot with anti-p53 antibody was preformed as well as a blot to act as a control for protein loading. The results obtained are depicted in FIG. 2(a). The bands corresponding to p53 protein and a loading control are indicated. Cells transfected with the pSUPER-p53 construct or empty pSUPER were analysed by flow cytometry. MCF-7 cells were transfected, irradiated (+IR, 10Gy) after 60 hours and analyzed 24 hours later for DNA content as described in Agami & Bernards (supra). The results obtained are depicted in FIG. 2(b) and cells with a G1-phase DNA content are indicated with an arrow.

The results obtained show that transfection of as little as 0.5 µg of pSUPER-p53 reduced p53 protein to very low levels and prevented entirely its induction following IR. When vector-transfected cells were irradiated, they arrested within 24 hours in either G1 or G2 with very few cells remaining in S phase. In contrast, cells transfected with the pSUPER-p53 almost completely lost their p53-dependent arrest in G1, but were able to establish a p53-independent G2/M arrest (FIG. 2b). These results indicate that the pSUPER-p53 vector can suppress the endogenous p53 to the extent that it abrogates the function of p53 in the DNA damage response.

The transfected cells were also studied by microscopy. FIG. 2(c) FIG. 2(c) shows cells transfected with 1 µg pSUPER vectors and 0.1 µg pBabe-puro plasmid which were selected with 1 µg/ml puromycin 48 hours later for 12 days. Plates were irradiated (20 Gy) and after 4 hours fixed and stained to detect p53. Shown also are the phase contrast images of the same colonies. The left and right images are of two different colonies.

Example 3

The ability of the methods of the invention to suppress the expression of a specific allele was assessed.

The CDH119 nt target-recognition sequence was mutated to give one basepair substitution at position 9 or 2 of the stem. Constructs capable of expressing each of the transcripts depicted in FIG. 3(a) were generated with the mutations highlighted in bold.

U2OS cells were transfected exactly as previously. Whole cell lysates were prepared after 60 hours, separated on 10% SDS-PAGE and analyzed by immunoblotting with anti-CDH1 antibody. Cyclin D1 protein was used to demonstrate equal loading. The results obtained are shown in FIG. 3(b). Empty pSUPER was constructed as a control as well as a construct capable of expressing GFP to determine transfection efficiency. The results obatined show that whilst the construct capable of generating a siRNA with complete sequence identity to the 19 nucleotide region of the Cdh1 gene could inhibit expression of Cdh1 as effectively as siRNA neither of the constructs with the point mutations were capable of inhibiting expression. This means that the constructs of the invention can discriminate between two alleles of the same gene inhibiting expression of one allele whilst allowing normal expression of the other.

Example 4

The ability of a the methods of the invention to inhibit the expression of a further gene, CDC20 was assessed.

FIG. 4 shows the sequences of the SiRNA and the predicted transcript of pSUPER-CDC20 utilized to inhibit CDC20 expression. The indicated SiRNAs and plasmids were transfected into MCF-7 cells as described above. Whole cell extracts were separated on 10% SDS-PAGE and immunoblotted to detect Cdc20 and Cyclin D1 proteins. The results show that the construct against CDC20 inhibited the desired gene and also that this inhibition is specific and not merely a non-specific response to dsRNA as transfection with the pSUPER-CDH1-B construct had no effect on CDC20 expression.

Example 5

Figure 5:
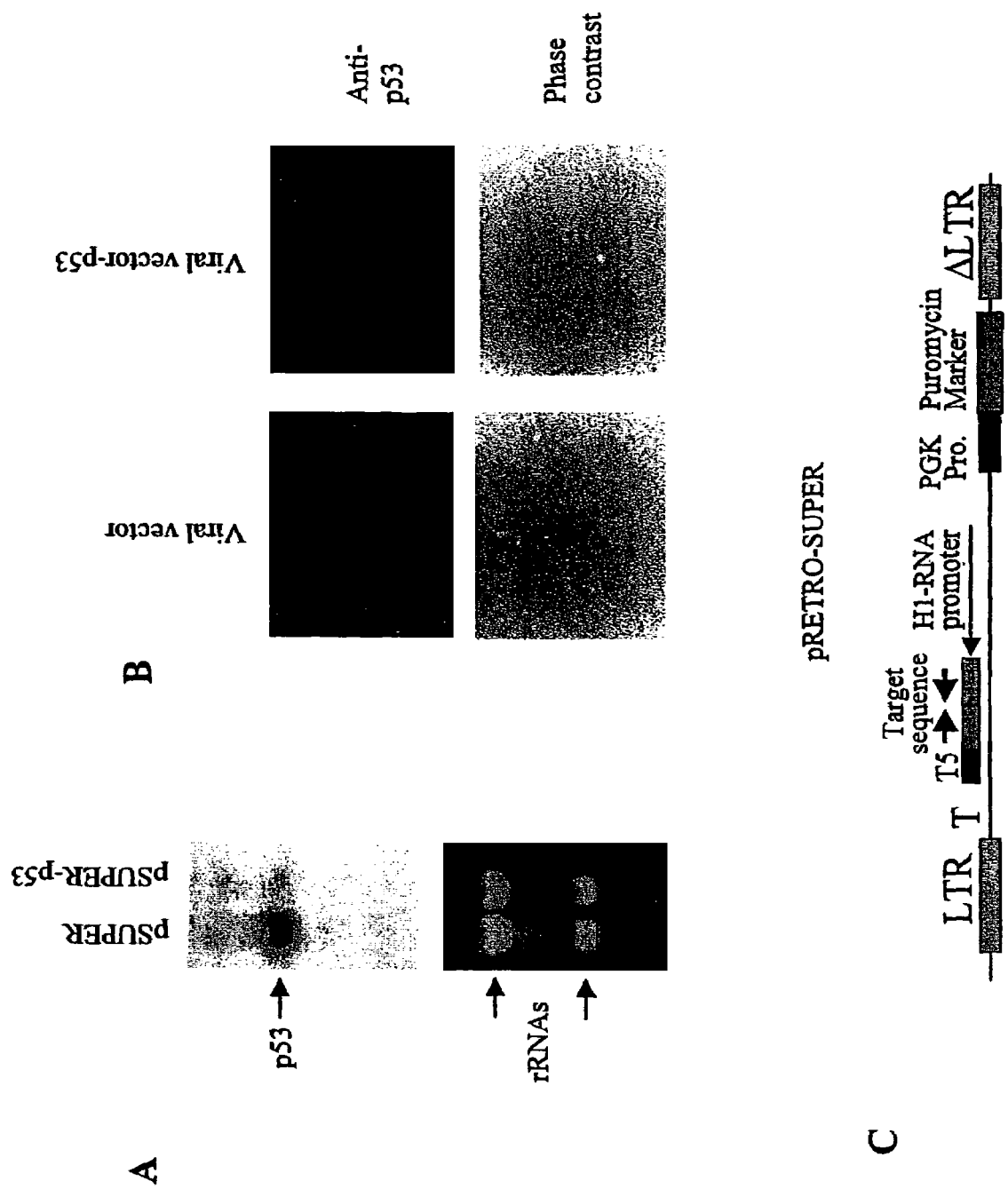
FIG. 5 shows the use of a vector of the invention to interfere with p53 mRNA expression.
Figure 6:
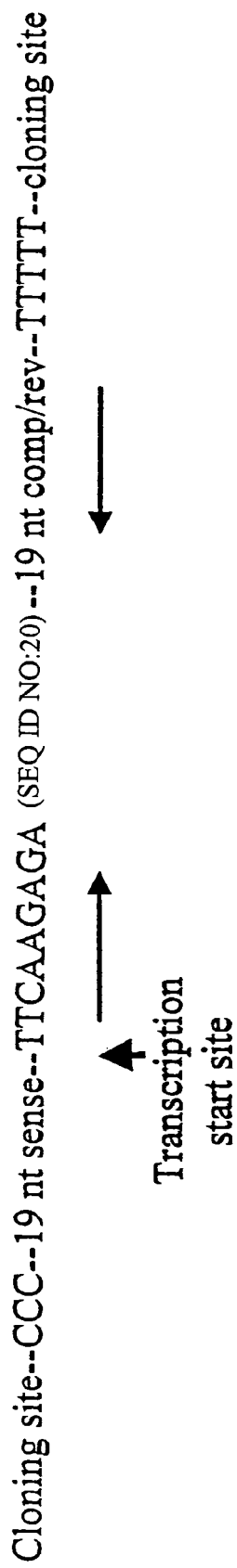
FIG. 6 shows a schematic representation of the various elements typically present in the construct of the invention. These are three consecutive cytosine residues, immediately after which transcription begins, the region encoding the siRNA, and the transcriptional terminator comprising 5 consecutive thymidine residues.

The effect of pSUPER-p53 vector on p53 mRNA stability was examined. MCF-7 cells were electroporated with pSUPER-p53 or vector and total RNA was extracted 48 hours later. Thirty µg of RNA was separated on agarose gel, blotted and probed with a p53 specific $^{32}P$ labeled probe. The rRNAs controls were visualized by Ethidium Bromide staining of the blot as a control for loading. The Northern blot obtained and control gel for rRNA loading are shown in FIG. 5(A). The cells transfected with the pSUPER-p53 vector have a substantially decreased level of p53 mRNA in comparison to cells transfected with the empty vector pSUPER.

siRNA interference mediated by the same stem-loop transcript can be expressed from retro viral vectors. Self-inactivating retro viral vectors (pRETRO-SUPER) expressing the puromycin marker gene were cloned to harbor either an empty pol-III promoter or one that targets p53 (see FIG. 2A) as depicted. The vector pRETRO-SUPER was constructed by restriction enzyme digestion of the self inactivating-retro viral vector (MSCVpuro) with EcoRI and XhoI and ligating to it the insert from the appropriate pSUPER plasmid digested with the same enzymes.

U2-OS cells containing the Ecotropic-receptor were infected three times with these vectors and one day later cells were selected for 4 days with 1 µg/ml puromycin and plated on glass slides. One day later, slides were irradiated (20 Gy), fixed four hours later and stained with anti-p53 antibody. Immno-florescence with a FITC-conjugated secondary antibody is shown together with the phase contrast of the same field. Both pictures were taken using the same settings of the camera and microscope. The resulting pictures are shown in FIG. 5(B).

A schematic drawing of the pRETRO-SUPER is given in FIG. 5(c) indicating the various elements present in the vector.

Figure 7:
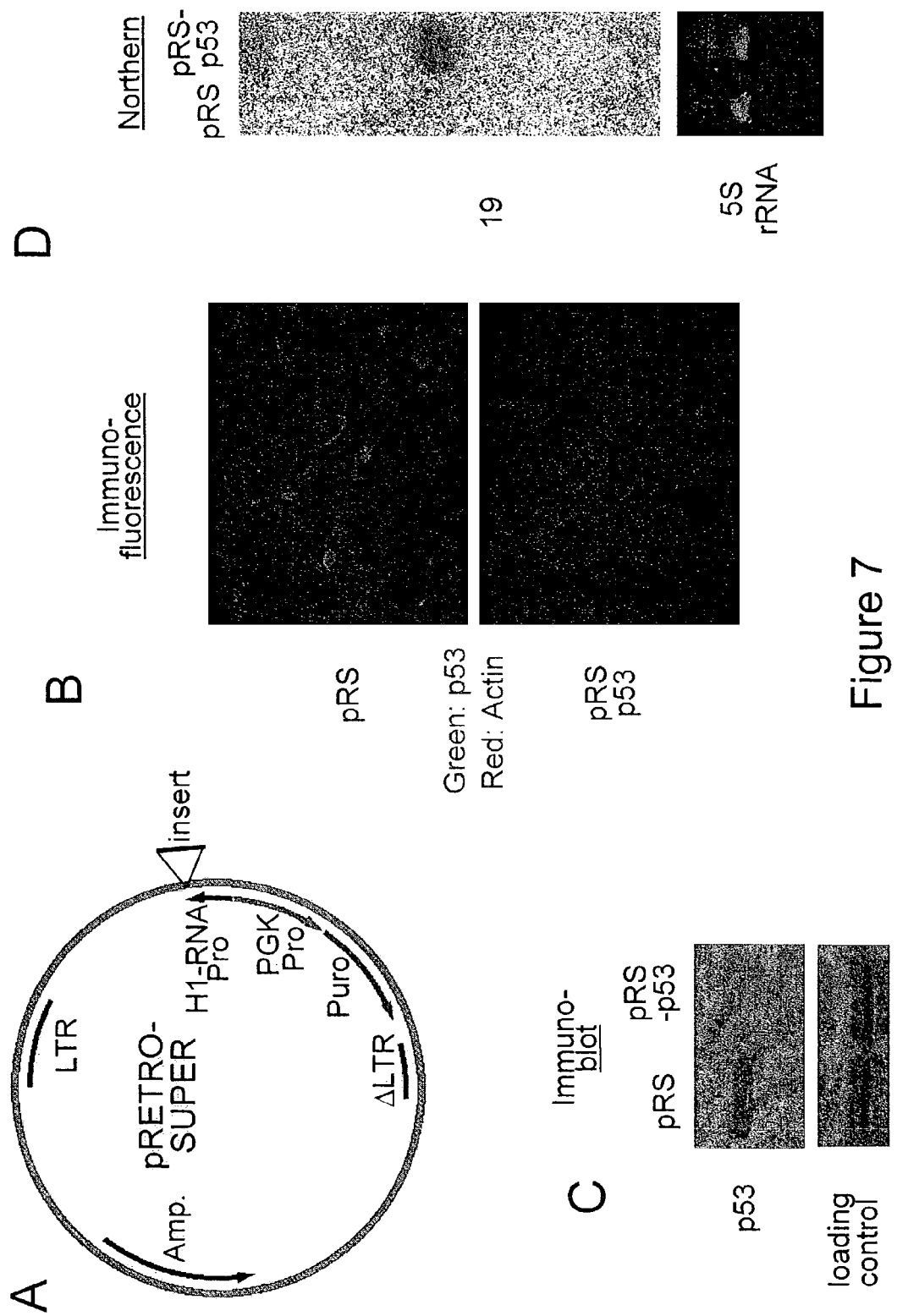
FIG. 7 shows the use of retroviral vectors to mediate RNA interference.

To accomplish more efficient delivery of short interfering RNAs, whether retroviruses that carry the pSUPER cassette can mediate gene silencing was tested. The entire pSUPER expression cassette from the p53 knockdown vector described in Example 2 was cloned into a self-inactivating pMSCV-puro retroviral vector. The 3' LTR of the murine stem cell virus (MSCV) was inactivated by an internal (NheI-XbaI) deletion to generate a self-inactivating virus (ΔLTR). Upon integration to the genome of the virus generated from this vector, the 3' ΔLTR is duplicated to the 5' LTR to generate a provirus that lacks all LTR's enhancer-promoter activities. The resulting vector, pRETRO-SUPER-p53 (pRS-p53), is shown in FIG. 7A.

Viral stocks were generated from this vector, and control pRETRO-SUPER vector, and used to infect U2-OS cells that express the murine ecotropic receptor to allow infection by ecotropic virus. After infection, cells were drug-selected and immuno-stained for p53 protein. FIG. 7B shows that the vast majority of the cells which were infected with the pRS-p53 virus stained only weakly for p53, whereas all of the pRS-control infected cells showed a clear nuclear p53 staining. As expected, the red staining of the control actin protein was similar in both polyclonal populations. Western blot analysis of these cells confirmed clear suppression of p53 expression mediated by pRS-p53 virus infection (FIG. 7C). Consistent with this, Northern blot analysis with the sense-19 nt p53 target sequence as a probe detected 21–22 nt siRNAs generated only by the pRS-p53 construct (FIG. 7D).

It was shown recently that RNA viruses are sensitive to RNA interference (Gitlin, et al, *Nature* 26, 26 (2002); Novina et al., *Nat Med* 8, 681–6. (2002); Jacque, et al, *Nature* 26, 26 (2002)). Nevertheless, high titer retroviral supernatants of pRS-p53 ($10^6$/ml) were obtained in spite of the fact that the full-length retroviral transcript produced by pRS-p53 also contains the p53 sequence that is targeted by the virally-encoded siRNAs. Apparently, the full-length retroviral transcript does not fall victim to self-inflicted RNA interference. One possible explanation could be that the intra-molecular base pairing of the p53 target sequence with its complementary sequence within the retroviral transcript precludes siRNA recognition. Alternatively, rapid packaging of retroviral transcript in a viral coat may render the full-length transcript relatively resistant to RNA interference. Whatever the explanation, these results indicate that retroviral vectors can be used to mediate efficient integration of pSUPER cassettes in human cells and direct the synthesis of siRNAs to suppress gene expression.

Example 6

To study the effects of inhibition of oncogenic RAS expression on the tumorigenic phenotype of human cancer cells, the expression of the endogenous mutant K-RAS$^{V12}$ allele was targeted with the pSUPER vector in the human pancreatic cell line CAPAN-1 (FIG. 8A). To target specifically the mutant K-RAS$^{V12}$ allele, a 19 nt targeting sequence spanning the region encoding valine 12 of mutant K-RAS was cloned into the pSUPER vector, yielding pSUPER-K-RAS$^{V12}$. The two oligos used to generate the pS-K-RAS$^{V12}$ are:

(SEQ ID NO:15)
5'gatccccGTTGGAGCTGTTGGCGTAGttcaagagaCTACGCCAACAGCTCCAACttttttggaaa3' and (SEQ ID NO:16)
5'agcttttccaaaaaGTTGGAGCTGTTGGCGTAGtctcttgaaCTACGCCAACAGCTCCAACggg3' where the 19 nt K-RAS$^{V12}$ target sequences are in capital letters and the G-T mutation that generates the Gly-Val substitution in amino acid 12 of K-RAS is in bold. These oligos were annealed to generate an insert with compatible ends to a BglII and HindIII digeted pSUPER vector. FIG. 8B shows that CAPAN-1 human pancreatic carcinoma cells transiently transfected with pSUPER-K-RAS$^{V12}$ had significant suppression of endogenous K-RAS$^{V12}$ expression, whereas control cyclin-D1 protein levels were unaffected (FIG. 8B).

The pSUPER-K-RAS$^{V12}$ cassette was then cloned into the pRETRO-SUPER retroviral vector of Example 5. pRS-K-RAS$^{V12}$ virus was then used to infect CAPAN-1 cells stably expressing the murine-ecotropic receptor (to allow retroviral infection). Parental pRS and pRS-p53 viral stocks were used for control infections. Following drug selection, a Western blot analysis with anti-K-RAS specific antibodies revealed that the K-RAS$^{V12}$ expression in the pRS-K-RAS$^{V12}$-infected CAPAN-1 cells was markedly suppressed compared to control infections (FIG. 8C).

Next, the specificity of the targeting construct was tested by examining the expression of wt K-RAS. EJ cells, which endogenously express two wild type K-RAS alleles, but harbor oncogenic H-RAS$^{V12}$ were used. Western blot analysis revealed that comparable levels of wt K-RAS protein were expressed in EJ cells, irrespective of whether they were infected with the same pRS-K-RAS$^{V12}$, pRS-p53 or pRS retroviral stocks used for the CAPAN-1 cells (FIG. 8D, lanes 1, 3, 4, 6). In contrast, p53 expression was suppressed equally by pRS-p53 in both EJ and CAPAN-1 cell types, ruling out the possibilities that the EJ cells were not infected or lacked components necessary for RNA interference (lanes 2 and 5). Thus, the RNA interference response provoked by the pRS-K-RAS$^{12}$ retrovirus is powerful and sufficiently selective to distinguish between the wild type and K-RAS$^{V12}$ alleles, which differ by one base pair only.

Figure 9:
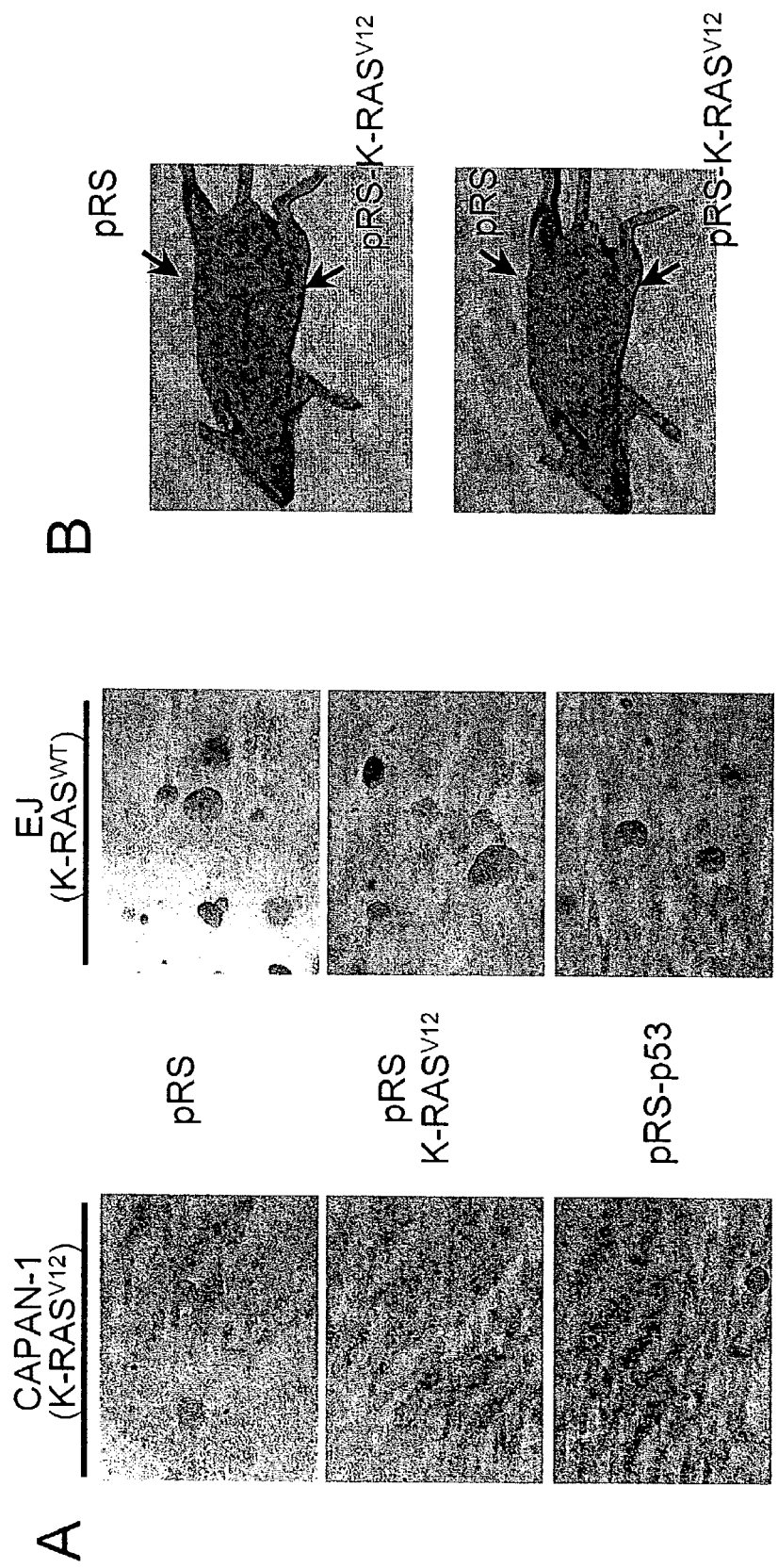
FIG. 9 shows stable and selective loss of tumorigenicity by a retroviral vector that targets the K-RAS$^{V12}$ oncogene. The same CAPAN-1 (harbor mutant K-RAS$^{V12}$) and EJ (harbor wild type K-RAS) cell populations as in FIG. 8 were infected with the indicated RETRO-SUPER viruses and selected for three days using 3 μg/ml puromycin.

The presence of oncogenic K-RAS alleles is frequent in human tumors, but almost invariably associated with multiple other genetic events. To address the question whether the oncogenic phenotype of late stage human tumors still depends on the expression of oncogenic mutant K-RAS, CAPAN-1 cells were again used. One phenotype that is associated with tumorigenicity is the ability to grow independent of anchorage when plated in a semi-solid media (soft agar assay). CAPAN-1 and EJ cells were infected with either pRS-K-RAS$^{V12}$ or with control pRS-p53 and pRS virus. After drug selection, $2 \times 10^4$ cells were plated in soft agar and allowed to grow for three weeks. As expected from transformed human tumor cell lines, both CAPAN-1 and EJ cell lines were able to grow and form colonies when infected with pRS and pRS-p53 control viruses (FIG. 8A and Table 1A). In contrast, infection of pRS-K-RAS$^{V12}$ abolished almost completely the colony growth of CAPAN-1 cells in this assay. Importantly, the effect of pRS-K-RAS$^{V12}$ was specific as soft agar growth of EJ cells (which contain the H-RAS$^{V12}$ oncogene) was unaffected (FIG. 9A and Table 1).

TABLE 1

| Cell line | PRS | pRS-K-RAS$^{V12}$ | pRS-p53 |
|---|---|---|---|
| CAPAN-1 | 150–200 | 0–2 | 150–200 |
| EJ | 300–400 | 300–400 | 300–400 |

Growth in soft agar. The average number of soft agar colonies from three independent experiments are represented.

Finally, we tested if down-regulation of K-RAS$^{V12}$ expression in CAPAN-1 cells affected their ability to form tumors in nude mice. CAPAN-1 cells were infected with either a pRS-K-RAS$^{V12}$ virus or pRS control virus and drug selected for three days to eliminate uninfected cells. After this, $1 \times 10^6$ infected cells were injected subcutaneously into athymic nude mice. As shown in FIG. 9B and Table 2, control pRS infected CAPAN-1 cells gave rise to tumors within 4 weeks in all mice, whereas none of the six animals infected with the pRS-K-RAS$^{V12}$ virus developed tumors.

TABLE 2

| Cell line: | PRS | pRS-K-RAS |
|---|---|---|
| CAPAN-1 | 6/6 | 0/6 |

Tumorigenicity in athymic nude mice of cells infected with K-RAS$^{V12}$ or control knockdown vector.

These results demonstrate for the first time that viral vectors can be used to integrate expression cassettes in the genomes of human cells, which mediate RNA interference to induce persistent loss-of function phenotypes. Vectors like these have at least two potential applications. In gene therapy, the selective down-regulation of only the mutant version of a gene allows for highly specific effects on tumor cells, while leaving the normal cells alone. This feature greatly reduces the need to design viral vectors with tumor-specific infection and/or expression. By designing target sequences that span chromosomal translocation breakpoints found in cancer, these vectors may also be used to specifically inhibit the chimeric transcripts of these translocated chromosomes. In addition, these vectors can be used to efficiently identify the genetic events that are required for cancer cells to manifest a tumorigenic phenotype. Through use of this technology, out of the many genetic alterations present in most human cancer cells, the most effective targets for drug development can be rapidly identified.

Example 7

This example relates to the integration of gene specific inserts of knock-down vectors into the genomic DNA of mammalian cells, the subsequent PCR amplification of such vectors, and the hybridisation of the amplification products on micro-arrays.

A micro-array containing 500 different 64-mer oligonucleotides corresponding to the sense and anti-sense strands of 250 gene specific bar code tags (encoding RNA hairpin molecules) was developed.

A 0.5 µg/µl oligonucleotide solution was used for spotting on polylysine coated glass slides. DNA was UV cross-linked to the arrays and the arrays were blocked using succenic anhydride treatment, denatured in boiling $H_2O$ and dried in 95% ethanol. Human U2OS cells expressing the murine ecotropic retroviral receptor were infected with a collection of 8 different siRNA expressing retroviruses (4 vectors directed against each of BLM and NBS1) and non-infected cells were eliminated using puromycin selection (for 48 hrs at 2 µg/ml final concentration). Genomic DNA was isolated of the retrovirally-infected human U2OS cells using DNA-zol reagent (Life Technologies) following the instructions of the manufacturer. Gene-specific bar codes were PCR amplified using primers forward (5'-cccttgaacctcctcgttcgacc-3') and reverse (5'-gagacgtgctacttccatttgtc-3') that were located up and downstream of the pSUPER cassette, resulting in a PCR fragment of around 600 base pairs. The PCR reaction was performed using 200 ng genomic DNA as a template with the Expand Long Template PCR system (Roche) following the instructions of the manufacturer and PCR buffer no. 3. These PCR products were fluorescently labelled using ULS Cy3 and Cy5 following instructions of the manufacturer (Kreatech, Amsterdam) and used as probes for the micro-array. The microarrays were first pre-hybridised in a buffer containing 5×SSC, 0.1% SDS and 1% BSA for 1 hrs at 42° C. Labelled PCR products were denatured and added to a hybridisation mixture (40 µl final volume) containing 20 µg Poly d(A), 8 µg yeast t-RNA 20 µg COT-1 DNA 25% formamide 5×SSC and 0.1% SDS. The hybridisation was done overnight at 42° C. Finally, the arrays were washed sequentially using initially 5×SSC/0.1% SDS, then 2×SSC/0.1% SDS, 1×SSC, 0.2×SSC and finally 0.05×SSC solutions.

Figure 10:
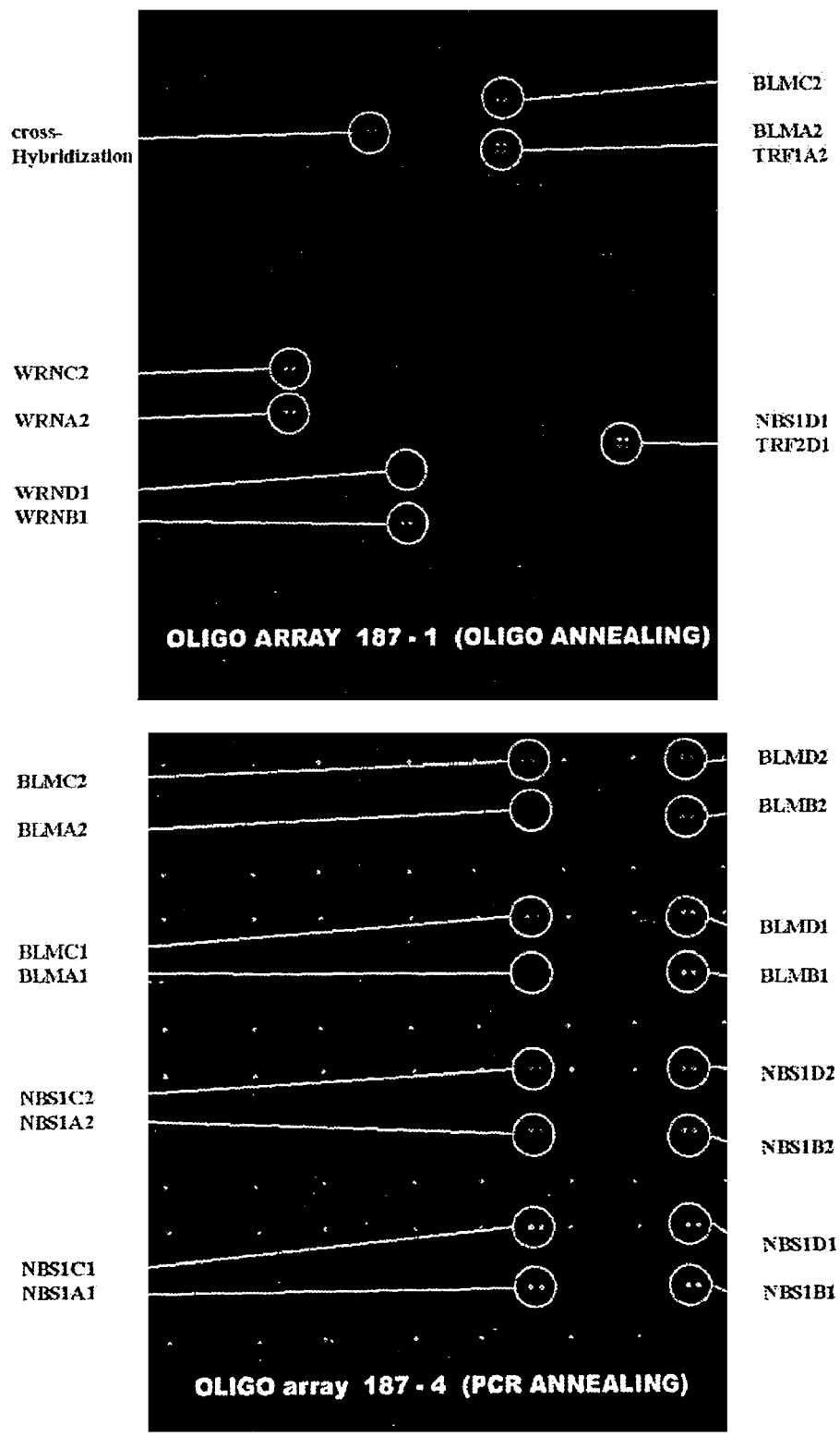
FIG. 10 shows the identification of "bar-coded" DNA fragments using oligonucleotide-containing micro-arrays. Both the sense strand (numbered 1) and anti-sense strands (numbered 2) of 64-mer oligonucleotides encoding short hairpin RNAs were spotted on polylysine-coated glass slides. In the upper panel (oligo array 187-1), hybridisation was done using a mixture of Cy3 or Cy5 labelled oligonucleotides. In the lower panel (oligo array 187-4), human cells were infected with knock-down vectors (against BLM, and NBS1, four knock-down vectors for each gene, A, B, C and D), genomic DNA was isolated, the knock-down cassettes were PCR amplified from genomic DNA, PCR products were labelled using Cy3 or Cy5 and hybridised to the oligonucleotide-containing micro-array.

This resulted in the predicted hybridisation pattern with virtually no cross-hybridisation (see FIG. 10). Both the sense strand (numbered 1) and anti-sense strand (numbered 2) 64-mer oligonucleotides encoding short hairpin RNAs were spotted on polylysine coated glass slides. In the upper panel (oligo array 187-1), hybridisation was done using a mixture of Cy3 or Cy5 labelled oligonucleotides. In the lower panel (oligo array 187-4), human cells were infected with knock-down vectors (against BLM, and NBS1, four knock-down vectors for each gene, A, B, C and D), genomic DNA was isolated, the knock-down cassettes were PCR amplified from genomic DNA, PCR products were labelled using Cy3 or Cy5 and hybridised to the oligonucleotide-containing micro-array.

Discussion

The fact that hybridisation of complex probe mixtures (e.g. cDNA) is very often done using micro-array technologies suggests strongly that the above technique can be extended to be carried out with greater numbers of vectors. Importantly, the self-complementary nature of the probe as well as of the spotted oligonucleotides on the micro-array does not prevent strong specific hybridisation signals. This also shows that hybridisation conditions exist that stimulate specific hybridisation of a mixture of bar code tags simultaneously.

The expression of polynucleotides of the invention in cells not only creates a gene-specific knock-down phenotype in such cells, but also introduces a gene specific fingerprint (bar code) in cells expressing these polynucleotides. In the polynucleotides of the invention, the region encoding an siRNA is unique in sequence and therefore introduction of such a polynucleotide into cells (e.g. mammalian cells) results in the creation of a tagged knock-down cell carrying a permanent gene-specific identifier. This molecular bar code is easily isolated by PCR amplification using PCR primers flanking the siRNA-encoding sequence. Labelling of the PCR product (e.g. fluorescently) allows identification of the tag by hybridisation to micro-arrays that contain the oligonucleotides that contain the gene-specific knockdown bar codes (these oligonucleotides must at least contain the gene-specific nucleotides).

The construction of a large collection of siRNA-encoding polynucleotides (for example in the form of expression vectors) makes it possible to carry out efficient loss of function genetic screens in mammalian cells. To assemble such a large collection, there must be at least one sequence in any given transcript that is unique to the transcript that is being targeted. This can be done by in silico BLAST search against the genome of interest. When the region complementary to the target gene is 19 nucleotides in length, to avoid cross-regulation of unintended targets, it is preferred to only select 19-mer sequences that have less than a 17 out of 19 identity with other unrelated transcripts. In addition, the GC content of each siRNA may be between 30–70%. This is to increase the chance that the knockdown vector/polynucleotide is active and to optimise hybridisation to oligonucleotide arrays. The 19 base transcript-specific sequence may be converted into a pair of complementary 64-mer oligonucleotides, which are then synthesised by standard synthesis techniques, annealed to from double stranded DNA and then individually cloned into the pSUPER vector or derivatives thereof.

As a result of the oligonucleotide design, this large collection of vectors/polynucleotides will contain molecular bar codes that are unique for each vector and have similar hybridisation properties due to their matching CG content. Following introduction into cells, the molecular bar code is easily isolated by PCR amplification using PCR primers. Where the polynucleotide is introduced by means of a vector, the PCR primers may flank the siRNA-encoding insert. When a large collection of such vectors/polynucleotides is expressed in a population of cells, PCR amplification of the bar codes will result in a mixture of bar code sequences corresponding to the mixture of knock-down vectors/polynucleotides that were introduced into the cell population. The relative abundance of each bar coded nucleic acid fragment in the cell population is influenced by the effect that each knockdown vector/polynucleotide has on cellular fitness under the experimental conditions. The relative abundance of each bar coded DNA fragment can be easily quantified using a DNA array consisting of bar code complementary DNA fragments. To do so, the PCR-amplified bar coded fragments can be labelled with a fluorescent dye (e.g. Cy5) and hybridised against bar coded DNA fragments PCR amplified from a control population of cells that harboured the same collection of knock-down vectors/ polynucleotide, but were not exposed to the biological signal of interest. This control population of bar coded DNA sequences can then be labelled with a different fluorescent dye (e.g. Cy3). Simultaneous hybridisation of the Cy5 and Cy3 labelled bar coded DNA fragments allows the identification of changes in relative abundance in the bar coded fragments that result from exposure of cells to a specific signal. The quantitative nature of DNA array hybridisation therefore allows the use of bar codes as knockdown identifiers to analyse large numbers of knockdown cells in parallel assays.

Genetic screens are powerful ways of identifying gene products that are causally involved in certain processes. Even in simple model organisms, genetic screens are often laborious and time-consuming because phenotypes need to be linked to genes. However, the method described herein allows simple and rapid identification of the cellular transcripts responsible for a selected biological phenotype. The method allows the identification of knockdown vectors/polynucleotides that are either positively- or negatively-selected in a population of cells that is subjected to a specific signal. In mammalian cells, polynucleotides/expression vectors of the invention can be used to generate loss of function phenotypes, and the unique bar coding of cells means that matching genes to phenotypes is rapid. Handling one batch of knock-down cells (in contrast to many single knock-down populations) can result in the identification of many knock-down phenotypes in a single experiment. Therefore, this technique allows high-throughput genetic analysis in a quick and cheap way. Potential applications for these bar code knock-down screens are for instance: (i) identification of genes that modify cellular fitness under conditions of stress (treatment of cells with any drug, UV light, growth factor deprivation, oncogene activation, etc), (ii) identification of synthetic lethal phenotypes (knock-down vectors that decrease cellular fitness specifically in the presence of a defined mutation such as mutant p53 or Retinoblastoma protein deficiency), (iii) identification of new genes in pathways (e.g. knock-downs lethal in normal cells but not in cells defective in the programmed cell death pathway, or TGF-β signalling, etc.).

Example 8

This example relates to the construction of a lentiviral vector, and its use in directing the synthesis of a p53-specific short hairpin transcript which mediates stable suppression of p53 expression through RNA interference.

Experimental Procedures

Plasmid Construction

The murine p53-specific short hairpin oligonucleotides were first cloned in pRETRO-SUPER (as described herein). pRETRO-SUPER vector was digested with BglII and HindIII and the annealed oligos targeting murine p53, 5'gatc-cccGTACATGTGTAATAGCTCCttcaa-gagaGGAGCTATTACACATGTACtttttgg aaa3' (SEQ ID NO:23) and 5'agcttttccaaaaGTACATGTGTAAT-AGCTCCtctcttgaaGGAGCTATTACACATGTACgg g-3' (SEQ id NO:24) were ligated with the vector, yielding pRETRO-SUPER-mp53. The 19-mer p53 targeting sequence in the oligonucleotide is indicated in capital letters. The lentiviral transfer vector HIV-CS-CG (Miyoshi, et al, (1998). J Virol 72, 8150–8157) was digested with EcoRI and XhoI to remove the CMV-GFP sequence. The cassette containing the H1 promoter and the p53 target sequence was excised from pSUPER-mp53 with EcoRI and XhoI and ligated, into HIV-CS to yield pLENTI-SUPER-p53.

Cell Culture, Lentiviral Production and Infection

Wild type FVB mouse embryonic fibroblasts (MEFs), ST.Hdh$^{Q111}$ mouse striatum cells (Trettel, et al, (2000). Hum Mol Genet 9, 2799–2809) and 293T cells were cultured in Dulbecco's modified Eagle's medium (DMEM) supplemented with 10% fetal calf serum. For production of lentivirus, 293T cells were transfected by the calcium-phosphate method using 10 μg transfer vector HIV-CS-CG or pLENTI-SUPER-mp53, 3.5 μg VSVg envelope vector pMD.G, 2.5 μg RSV-Rev and 6.5 μg packaging vector pCMV☐R8.2 (Miyoshi, et al, (1998). J Virol 72, 8150–8157). Lentiviruses were harvested 24 hours and 48 hours after transfection and filtered through a 0.45 μM filter. ST.Hdh$^{Q111}$ cells were shifted to 39° C. 14 days prior to lentiviral infection. WT MEFs were cultured to passage 9–10 whereupon cells were counted every 3–4 days 14 days prior to lentiviral infection. The senescent phenotype was also investigated by acidic β-galactosidase staining at the time of infection (Dimri, et al, (1995). Proc Natl Acad Sci U S A 92, 9363–9367). $1.8 \times 10^5$ senescent WT MEFs in 6 cm dishes were infected with lentivirus for at least 12 hours in the presence of 0.8 μg/ml polybrene, and were then allowed to recover for 48 hours before reseeding for colony formation assays and growth curves. $0.5 \times 10^5$ or $1 \times 10^5$ cells were seeded in 10 cm dishes for colony formation assays. Cells were fixed and stained with superstain (50% Methanol, 10% Acetic acid, 0.1% Comassie Blue) 16 days after seeding. For growth curves $1.5 \times 10^3$ cells were seeded per 3.5 cm dish, at three-day intervals cells were fixed with 0.5% formaldehyde, stained with 0.1% crystal violet followed by re-solubilisation in 10% acetic acid. The $OD_{590}$ was quantified as a relative measure of cell number.

Western Blot Analysis

Whole cell extracts were separated on 12% SDS-PAGE gels and transferred to polyvinylene diflouride membranes (Millipore). Visualisation was done using enhanced chemiluminescence (Amersham Biosciences, Inc.). Antibodies used were M-156 (Santa Cruz) against p16$^{INK4a}$, ab80-50 (Abcam) against 19$^{ARF}$, F-5 (Santa Cruz) against p21, Ab-7 (Oncogene) against p53 and P30620 (Transduction labs) against PAI-1.

Time-Lapse Microscopy $5 \times 10^4$ senescent MEFs were seeded in 3.5 cm dishes and infected with lentivirus. Time-lapse microscopy was initiated 234 hours after infection in a temperature and $CO_2$-controlled chamber using 10×phase contrast. Frames were taken every 20 minutes over a period of 38 hours.

Results and Discussion.

A lentiviral derivative of the pRETRO-SUPER vector described herein was generated by cloning the H1 RNA short hairpin gene expression cassette targeting murine p53 from pRETRO-SUPER into the self-inactivating lentiviral vector pHIV-CS (Miyoshi, et al, (1998). J Virol 72, 8150–8157). This vector was named pLENTI-SUPER-p53 (FIG. 11A). As a control, a lentiviral vector that expresses GFP (HIV-CS-CG) (Miyoshi, et al, (1998). J Virol 72, 8150–8157) was used.

Loss of p53 in primary mouse embryo fibroblasts is associated with acquisition of an immortal phenotype (Harvey, et al, (1993). Oncogene 8, 2457–2467). To test whether the lentiviral p53 knockdown vector was capable of inducing a functional inactivation of p53 in mouse embryo fibroblasts (MEFs), early-passage primary MEFs were infected with LENTI-SUPER-p53 virus or with control GPF lentivirus, and immortalisation monitored to indicate p53 knockdown. GFP staining of control-virus infected cells indicated that some 30–40% of the primary MEFs were successfully infected (data not shown). FIG. 11B and C show that infection with LENTI-SUPER-p53, but not with control GFP lentiviral vector, caused efficient immortalisation of the infected primary MEFs, indicating that the LENTI-SUPER-p53 virus mediates functional inactivation of p53 expression (see also FIG. 13A).

Figure 12:
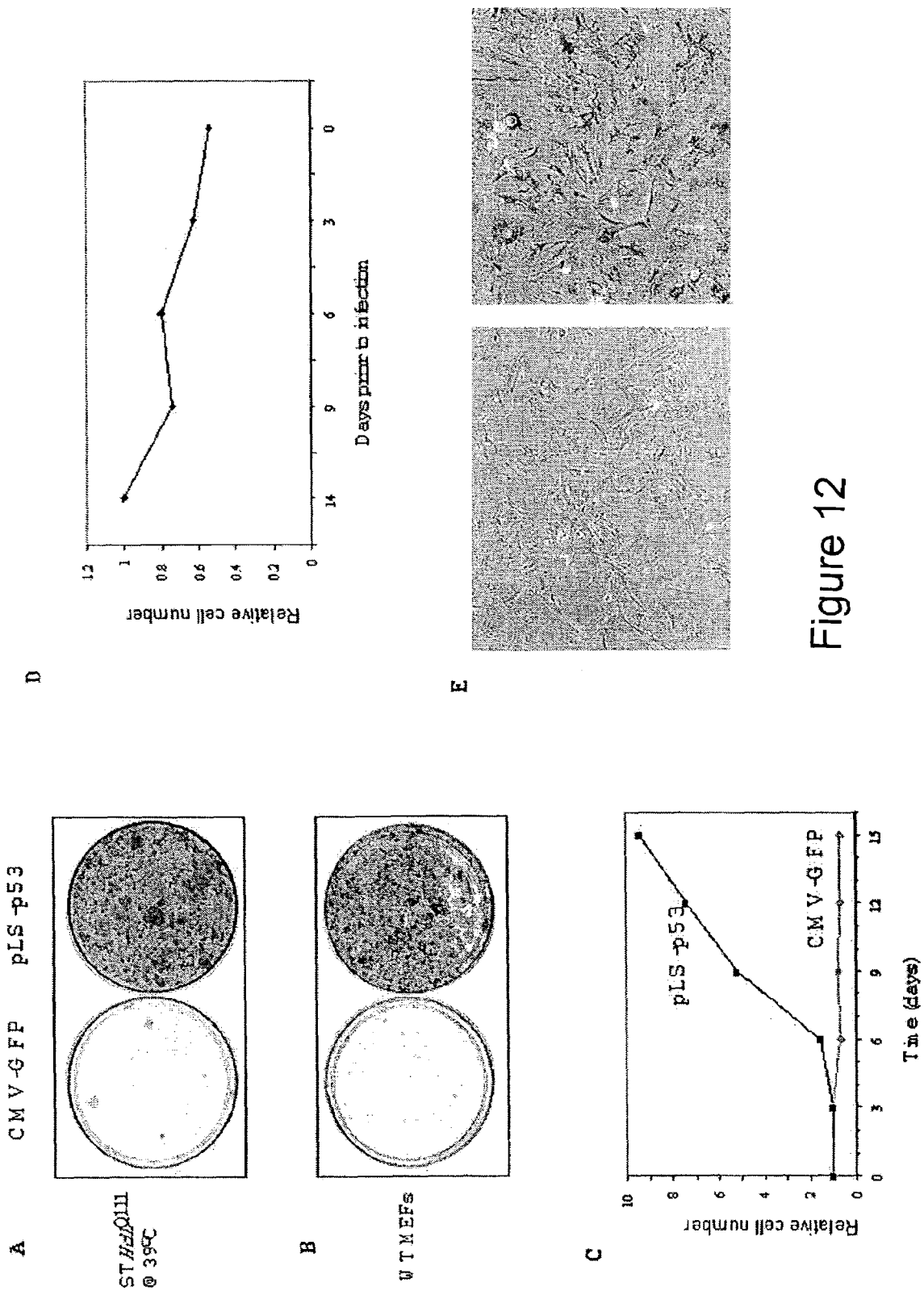
FIG. 12 shows Lentivirus-mediated p53 suppression reverses senescence. A: STHdh$^{Q111}$ cells were shifted to the non-permissive temperature of 39.5° C. at which T antigen is inactive and were kept for 14 days to assure that all cells were senescent prior to infection with CMV-GFP or pLS-p53 lentivirus. $5 \times 10^4$ cells were seeded for colony formation assays and dishes were stained 2 weeks later. B: Senescent MEFs infected with CMV-GFP or pLS-p53 lentivirus were seeded at $1 \times 10^5$ cells per 10 cm dish and dishes were stained 16 days after seeding. C: 48 hours after infection with CMV-GFP (gray) or pLS-p53 (black), 1.5×10³ cells were seeded per well in six-well dishes. At three-day intervals cells were fixed and stained with crystal violet and quantified by determining $OD_{590}$ as a relative measure of cell number. D: WT MEFs were cultured to passage 9. Fourteen days prior to lentiviral infection cells were counted and equal numbers of cells were replated every 3 days. E: Immediately prior to lentiviral infection, passage 5 and senescent WT MEFs were subjected to acidic β-galactosidase staining (Dimri, et al, (1995). Proc Natl Acad Sci U S A 92, 9363–9367). Cells were fixed with 0.5% glutaraldehyde and incubated with staining solution overnight at 37° C.

Next, whether suppression of p53 expression by lentiviral gene transfer in senescent cells would allow re-entry into the cell cycle was examined. Two cell systems were employed to address this question. First, conditionally immortalized STHdh$^{Q111}$ neuronal cells derived from mouse embryonic striatum were used. These cells are conditionally immortalised due to the presence of a temperature sensitive allele of SV40 T antigen (Trettel, et al, (2000). Hum Mol Genet 9, 2799–2809). STHdh$^{Q111}$ cells proliferate indefinitely at the permissive temperature (32° C.), but rapidly and synchronously become post-mitotic and adopt a senescent morphology when shifted to the non-permissive temperature (39.5° C.) at which T antigen is inactive (Brummelkamp, et al, (2002). J Biol Chem 277, 6567–6572). STHdh$^{Q111}$ cells that had been maintained at 39.5° C. for two weeks were used to assure that the entire population was senescent, and the senescent cells were then infected with the LENTI-SUPER-p53 virus or control GFP lentivirus. The infected cells were maintained at 39.5° C. for two weeks. FIG. 12A shows that knockdown of p53 led to re-entry into the cell cycle and allowed continued proliferation, indicating that the senescence-like growth arrest of STHdh$^{Q111}$ cells at the non-permissive temperature can be reversed by suppression of p53.

Figure 13:
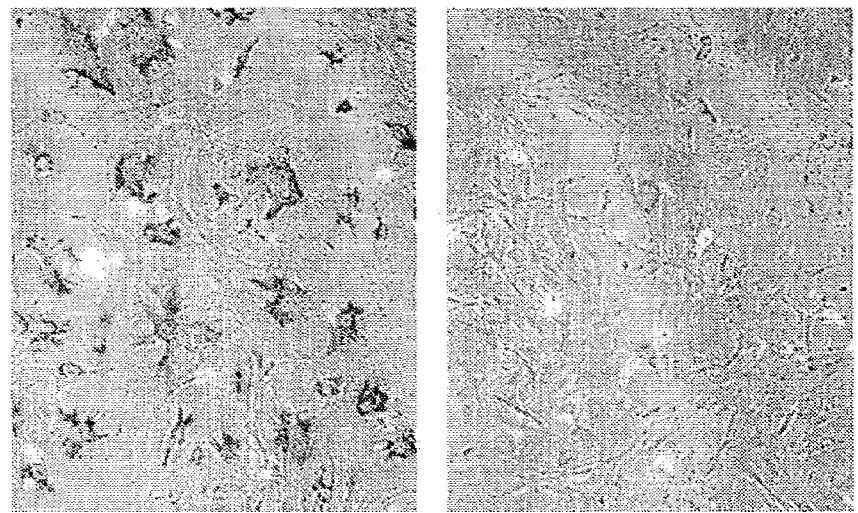
FIG. 13 shows senescence markers in reverted WT MEFs. A: Western blots of senescence markers in passage 3 (lane 1), senescent (lane 2) and WT MEFs reverted from senescence by knockdown of p53 (lane 3). B: Acidic P-galactosidase staining performed on senescent and reverted WT MEFs (as described in the legend to FIG. 12).
Figure 13:
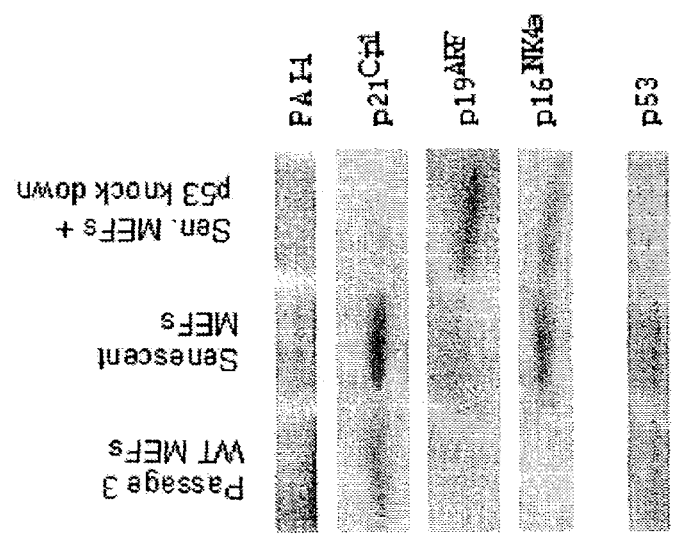

Next, whether p53 knockdown would allow cell cycle re-entry in senescent primary MEFs was examined. Primary MEFs of FVB genotype were cultured until the cells no longer proliferated (FIG. 12D) and expressed high levels of the senescence-associated markers acidic β-galactosidase, PAI-1, p21$^{cip1}$, p19$^{ARF}$ and p16$^{INK4a}$ (FIGS. 12E, 13A). All cells in the culture showed a flat senescent morphology and stained intensely for acidic β-galactosidase (FIG. 12E), indicating that these cells were quantitatively senescent. This notion is also supported by the growth curves of these late-passage MEFs, which showed a constant decline in cell number over time (FIG. 12D), indicative of the absence of spontaneously-immortalised cells in the culture. FIGS. 12B and C show that lentiviral knockdown of p53 in these senescent primary MEF cultures triggered a marked degree of proliferation. Importantly, cell cycle re-entry was associated with loss of expression of several of the senescence-associated markers, including PAI-1, p21$^{cip1}$ and acidic β-galactosidase (FIG. 13A, B) and senescence-reverted cells continued to proliferate for several weeks without any signs op senescence, suggesting that they had become immortal (FIG. 12B and data not shown).

Figure 14:
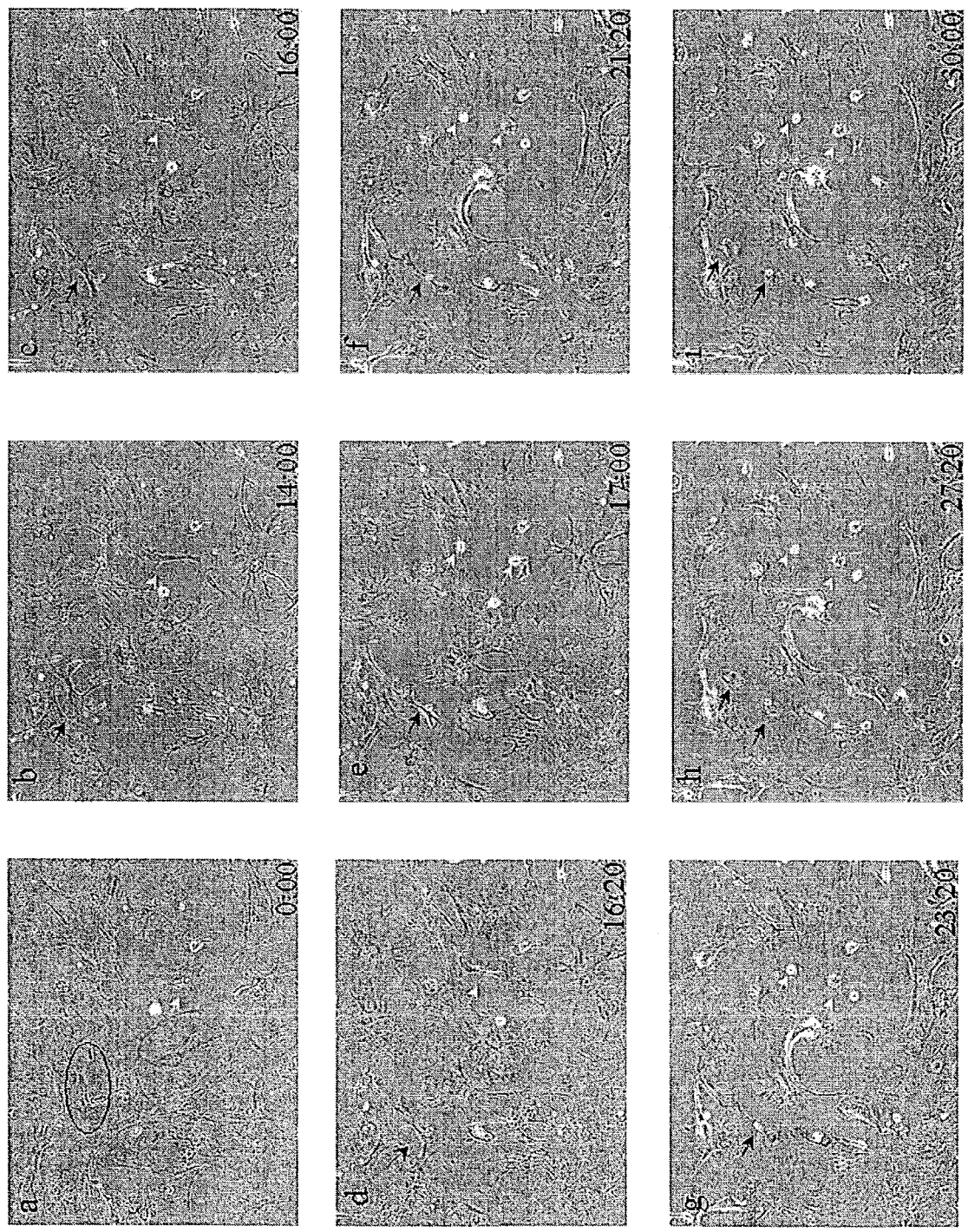
FIG. 14 shows time lapse microscopy of senescent MEFs following knockdown of p53. Selected frames from a 38 hour recording period of senescent WT MEFs infected with LENTI-SUPER-p53. Time points are indicated in the lower right corner of individual frames. A cell undergoing successful division is indicated with a black ring and black arrows while a division immediately followed by apoptosis is indicated with white arrows.

In principle, the observed proliferation following lentiviral knockdown of p53 could originate from cells that were not truly senescent in the culture. It was therefore important to follow the cultures of senescent MEFs in time after lentiviral infection. FIG. 14 shows a series of time-lapse photomicrographs of senescent MEFs after lentiviral knockdown of p53, which together indicate that cells with a completely flat and senescent morphology round up and divide within a 48-hours after infection with the p53 knockdown virus (FIG. 14, cells marked by black arrows). However, not all cell divisions are productive as many cells divide initially, but die by apoptosis during division or just after completion of cell division (FIG. 14, cells marked by white arrows). No division or apoptosis could be observed following infection with control lentivirus encoding GFP (data not shown). It can be concluded that cells with all the hallmarks of fully senescent cells rapidly re-enter the cell cycle after p53 knockdown. It can also be concluded that p53 is not only required to initiate senescence, but is also required, at least in MEFs, to maintain senescence.

Evidence is provided that suppression of p53 expression in senescent MEFs leads to a reversion of the senescent state and causes immortalisation. Several lines of evidence support the notion that the MEFs were fully senescent at the time of infection with the lentiviral p53 knockdown vector. First, the cells had stopped proliferating in the presence of growth factors, indicating that they were senescent and refractory to growth factor stimulation, rather than quiescent and still responsive to growth factors (FIG. 11D). Second, they uniformly manifested a senescent morphology and expressed the senescence-associated markers acidic β-galactosidase, PAI-1, p21$^{cip1}$, p19$^{ARF}$ and p16$^{INK4a}$ (FIGS. 12E, 13A). When cells emerged from senescence as a result of p53 knockdown, the cells behaved phenotypically as p53 null MEFs in that they were immortal, had low levels of p21$^{cip1}$ and high levels of p19$^{ARF}$ (Harvey, et al, (1993). Oncogene 8, 2457–2467; Kamijo, et al, (1997). Cell 91, 649–659; Zindy, et al, (1998). Genes Dev 12, 2424–2433). Importantly, the cells that emerged from senescence by p53 knockdown maintained high levels of p16$^{INK4a}$ (FIG. 13A). As p16$^{INK4a}$ expression is induced during senescence in a p53-independent fashion (Zindy, et al, (1998). Genes Dev 12, 2424–2433), these data indicate that the signaling pathways that led to the induction of senescence are still operational in senescence-reverted MEFs. This provides further evidence that the cells that re-entered cell cycle by p53 knockdown were indeed fully senescent at the time of infection with the p53 knockdown virus.

These data are in agreement with earlier experiments performed in senescent human diploid fibroblasts. Thus, ablation of p53 function by microinjection of p53 antibody in primary human fibroblasts allowed at least temporary reversal of senescence and re-entry into the cell cycle (Gire & Wynford-Thomas, (1998). Mol Cell Biol 18, 1611–1621). However, inactivation of p53 in human fibroblasts delays, but does not abrogate replicative senescence, indicating that p53 inactivation alone is not sufficient to mediate stable reversion of senescence in primary human fibroblasts and requires also induction of hTERT expression (Itahana, et al, (2001). Eur J Biochem 268, 2784–2791; Shay, et al (1991). ExpCell Res 196, 33–39). A feature of the lentiviral vector system described here is that suppression of gene expression is persistent, allowing the study of long-term consequences of gene inactivation in post-mitotic cells. The LENTI-SUPER vector is therefore a useful tool to investigate which genes are continuously required to maintain a post-mitotic state in cells that have exited the cell cycle. The signaling pathways that lead to the induction of a post mitotic (terminally differentiated) state are well-studied, but the genes and pathways required to maintain such a post mitotic state are poorly understood. The vector system described in this example was developed to silence gene expression in non-dividing cells and was used to study the genes that are required for the maintenance of senescence. It was found that p53 is essential to maintain senescence, as senescent cells in which p53 expression is suppressed rapidly re-enter the cell cycle to become immortal. This vector system is broadly applicable to study the genes that are required to maintain a post mitotic state in cells that have exited the cell cycle.

SEQUENCE LISTING

<160> NUMBER OF SEQ ID NOS: 25

<210> SEQ ID NO 1
<211> LENGTH: 1057
<212> TYPE: DNA
<213> ORGANISM: Homo sapiens

<400> SEQUENCE: 1

| ttataggag ctgaagggaa ggggtcaca gtaggtggca tcgttccttt ctgactgccc | 60 |
| gcccccgca tgccgtcccg cgatattgag ctccgaacct ctcgccctgc cgccgccggt | 120 |
| gctccgtcgc cgccgcgccg ccatggaatt cgaacgctga cgtcatcaac ccgctccaag | 180 |
| gaatcgcggg cccagtgtca ctaggcggga acacccagcg cgcgtgcgcc ctggcaggaa | 240 |
| gatggctgtg agggacaggg gagtggcgcc ctgcaatatt tgcatgtcgc tatgtgttct | 300 |
| gggaaatcac cataaacgtg aaatgtcttt ggatttggga atcttataag ttctgtatga | 360 |
| gaccactctt tcccataggg cggagggaag ctcatcagtg gggccacgag ctgagtgcgt | 420 |
| cctgtcactc cactcccatg tcccttggga aggtctgaga ctagggccag aggcggccct | 480 |
| aacagggctc tccctgagct tcggggaggt gagttcccag agaacggggc tccgcgcgag | 540 |
| gtcagactgg gcaggagatg ccgtggaccc cgcccttcgg ggaggggccc ggcggatgcc | 600 |
| tcctttgccg gagcttggaa cagactcacg gccagcgaag tgagttcaat ggctgaggtg | 660 |
| aggtaccccg caggggacct cataacccaa ttcagactac tctcctccgc ccattttttgg | 720 |
| aaaaaaaaaa aaaaaaaaaa aacaaaacga aaccggccg gcgcggtgg ttcacgccta | 780 |
| taatcccagc actttgggag gccgaggcgg gcggatcaca aggtcaggag gtcgagacca | 840 |
| tccaggctaa cacggtgaaa ccccccccca tctctactaa aaaaaaaaaa tacaaaaaat | 900 |
| tagccattag ccgggcgtgg tggcgggcgc ctataatccc agctacttgg gaggctgaag | 960 |
| cagaatggcg tgaacccggg aggcggacgt tgcagtgagc cgagatcgcg ccgactgcat | 1020 |
| tccagcctgg gcgacagagc gagtctcaaa aaaaaa | 1057 |

<210> SEQ ID NO 2
<211> LENGTH: 229
<212> TYPE: DNA
<213> ORGANISM: Homo sapiens

<400> SEQUENCE: 2

| gaattcgaac gctgacgtca tcaacccgct ccaaggaatc gcgggcccag tgtcactagg | 60 |
| cgggaacacc cagcgcgcgt gcgccctggc aggaagatgg ctgtgaggga caggggagtg | 120 |
| gcgccctgca atatttgcat gtcgctatgt gttctgggaa atcaccataa acgtgaaatg | 180 |
| tctttggatt tgggaatctt ataagttctg tatgagacca ctctttccc | 229 |

<210> SEQ ID NO 3
<211> LENGTH: 21
<212> TYPE: DNA
<213> ORGANISM: Artificial sequence
<220> FEATURE:
<223> OTHER INFORMATION: Sense strand of the synthetic siRNA against Cdh1 depicted in Figure 1(b).
<220> FEATURE:
<221> NAME/KEY: misc_feature
<222> LOCATION: (20)..(21)
<223> OTHER INFORMATION: n = t

<400> SEQUENCE: 3
ugagaagucu cccagucagn n                                          21

<210> SEQ ID NO 4
<211> LENGTH: 21
<212> TYPE: DNA
<213> ORGANISM: Artificial sequence
<220> FEATURE:
<223> OTHER INFORMATION: Antisense strand of the synthetic siRNA
      against Cdh1 depicted in Figure 1(b).
<220> FEATURE:
<221> NAME/KEY: misc_feature
<222> LOCATION: (20)..(21)
<223> OTHER INFORMATION: n = t

<400> SEQUENCE: 4
cugacuggga gacuucucan n                                          21

<210> SEQ ID NO 5
<211> LENGTH: 47
<212> TYPE: RNA
<213> ORGANISM: Artificial sequence
<220> FEATURE:
<223> OTHER INFORMATION: Sequence of the predicted stem loop transcript
      generated from pSU PER-Cdh11-A depicted in Figure 1(b).

<400> SEQUENCE: 5
ugagaagucu cccagucagc agagcucuga cugggagacu ucucauu              47

<210> SEQ ID NO 6
<211> LENGTH: 49
<212> TYPE: RNA
<213> ORGANISM: Artificial sequence
<220> FEATURE:
<223> OTHER INFORMATION: Sequence of the predicted stem loop transcript
      generated from pSU PER-Cdh11-B depicted in Figure 1(b).

<400> SEQUENCE: 6
ugagaagucu cccagucagu ucaagagacu gacugggaga cuucucauu            49

<210> SEQ ID NO 7
<211> LENGTH: 45
<212> TYPE: RNA
<213> ORGANISM: Artificial sequence
<220> FEATURE:
<223> OTHER INFORMATION: Sequence of the predicted stem loop transcript
      generated from pSU PER-Cdh11-C depicted in Figure 1(b).

<400> SEQUENCE: 7
ugagaagucu cccagucagu ucgacugacu gggagacuuc ucauu                45

<210> SEQ ID NO 8
<211> LENGTH: 49
<212> TYPE: RNA
<213> ORGANISM: Artificial sequence
<220> FEATURE:
<223> OTHER INFORMATION: Sequence of the predicted stem loop transcript
      generated from pSU PER-p53 which is also depicted in Figure 2(a).

<400> SEQUENCE: 8
gacuccagug guaaucuacu ucaagagagu agauuaccac uggagucuu            49

Figure 3:
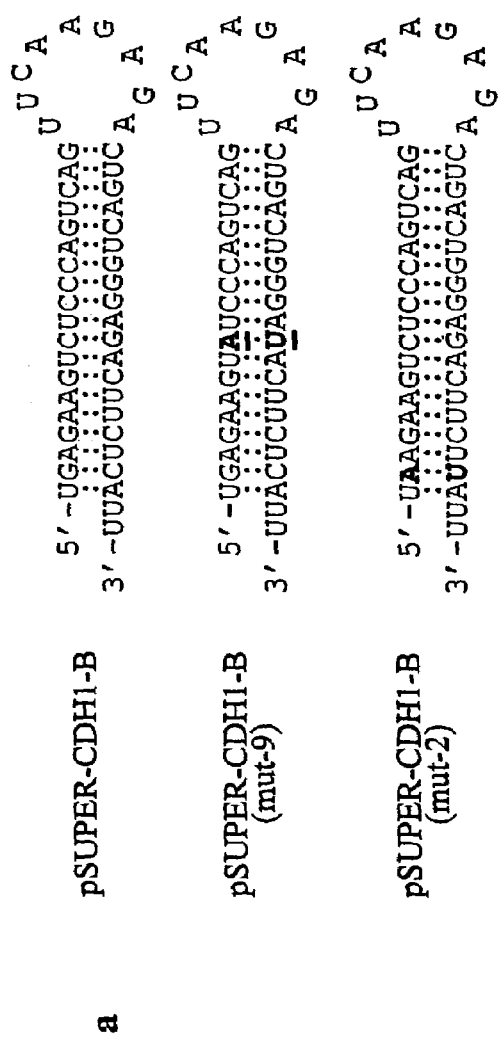
FIG. 3(a) depicts the intact target recognition sequence required to suppress CDH1 by the pSUPER-CDH1 vector. The CDH119 nucleotide target-recognition sequence was mutated to give one basepair substitution at position 9 or 2 of the stem. The predicted secondary structures of the transcripts are shown (mutations are in bold and underlined).
FIG. 3(b) shows an immunoblot against CDH1 of cells transfected with the constructs displayed in FIG. 3(a) probed with anti-CDH1 antibody. Cyclin D1 protein was used to demonstrate equal loading.
Figure 3:
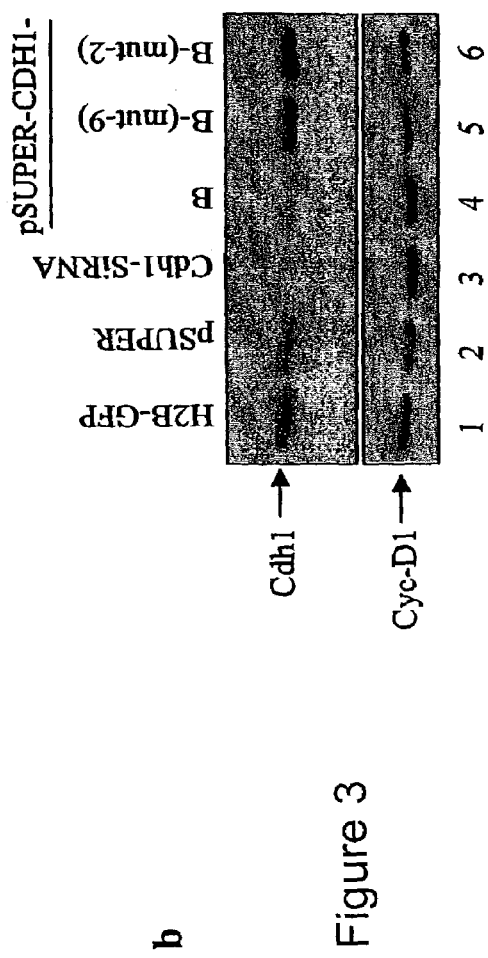

<210> SEQ ID NO 9
<211> LENGTH: 49
<212> TYPE: RNA
<213> ORGANISM: Artificial sequence
<220> FEATURE:
<223> OTHER INFORMATION: Sequence of the predicted stem loop transcript
      generated from the pUPER-Cdh11-B vector as depicted in Figure 3

(a).

<400> SEQUENCE: 9
ugagaagucu cccagucagu ucaagagacu gacugggaga cuucucauu     49

<210> SEQ ID NO 10
<211> LENGTH: 49
<212> TYPE: RNA
<213> ORGANISM: Artificial sequence
<220> FEATURE:
<223> OTHER INFORMATION: Sequence of the predicted stem loop transcript
      generated from the pSUPER-Cdh11-B(mut-9) vector as depicted in
      Figure 3(a).

<400> SEQUENCE: 10
ugagaaguau cccagucagu ucaagagacu gacugggaua cuucucauu     49

<210> SEQ ID NO 11
<211> LENGTH: 49
<212> TYPE: RNA
<213> ORGANISM: Artificial sequence
<220> FEATURE:
<223> OTHER INFORMATION: Sequence of the predicted stem loop transcript
      generated from the pSUPER-Cdh11-B(mut-2) vector as depicted in
      Figure 3(a).

<400> SEQUENCE: 11
uaagaagucu cccagucagu ucaagagacu gacugggaga cuucuuauu     49

<210> SEQ ID NO 12
<211> LENGTH: 21
<212> TYPE: DNA
<213> ORGANISM: Artificial sequence
<220> FEATURE:
<223> OTHER INFORMATION: The sequence of the sense strand of the
      synthetic siRNA against CDC20 depicted in Figure 4.
<220> FEATURE:
<221> NAME/KEY: misc_feature
<222> LOCATION: (20)..(21)
<223> OTHER INFORMATION: n = t

<400> SEQUENCE: 12
cggcaggacu ccgggccgan n                                   21

<210> SEQ ID NO 13
<211> LENGTH: 21
<212> TYPE: DNA
<213> ORGANISM: Artificial sequence
<220> FEATURE:
<223> OTHER INFORMATION: Sequence of the antisense strand of the
      synthetic siRNA against CDC20 depicted in Figure 4.
<220> FEATURE:
<221> NAME/KEY: misc_feature
<222> LOCATION: (20)..(21)
<223> OTHER INFORMATION: n = t

<400> SEQUENCE: 13
ucggcccgga guccugccgn n                                   21

<210> SEQ ID NO 14
<211> LENGTH: 49
<212> TYPE: RNA
<213> ORGANISM: Artificial sequence
<220> FEATURE:
<223> OTHER INFORMATION: Sequence of the predicted stem loop transcript
      generated from the pSUPER-CDC20 vector as depicted in Figure 4.

<400> SEQUENCE: 14
cggcaggacu ccgggccgau ucaagagauc ggcccggagu ccugccguu          49

<210> SEQ ID NO 15
<211> LENGTH: 64
<212> TYPE: DNA
<213> ORGANISM: Artificial sequence
<220> FEATURE:
<223> OTHER INFORMATION: Oligonucleotide used to generate pS-K-RASV12.

<400> SEQUENCE: 15
gatccccgtt ggagctgttg gcgtagttca agagactacg ccaacagctc caacttttg          60 gaaa          64

<210> SEQ ID NO 16
<211> LENGTH: 64
<212> TYPE: DNA
<213> ORGANISM: Artificial sequence
<220> FEATURE:
<223> OTHER INFORMATION: Oligonucleotide used to generate pS-K-RASV12.

<400> SEQUENCE: 16
agcttttcca aaaagttgga gctgttggcg tagtctcttg aactacgcca acagctccaa          60
cggg          64

<210> SEQ ID NO 17
<211> LENGTH: 19
<212> TYPE: DNA
<213> ORGANISM: Homo sapiens

<400> SEQUENCE: 17
gttggagctg gtggcgtag          19

<210> SEQ ID NO 18
<211> LENGTH: 19
<212> TYPE: DNA
<213> ORGANISM: Homo sapiens

<400> SEQUENCE: 18
gttggagctg ttggcgtag          19

<210> SEQ ID NO 19
<211> LENGTH: 49
<212> TYPE: RNA
<213> ORGANISM: Artificial sequence
<220> FEATURE:
<223> OTHER INFORMATION: Sequence of the predicted stem loop transcript
      generated from the pSUPER-K-RASV12 vector as depicted in Figure
      8A.

<400> SEQUENCE: 19
guuggagcug uuggcguagu ucaagagacu acgccaacag cuccaacuu          49

<210> SEQ ID NO 20
<211> LENGTH: 9
<212> TYPE: DNA
<213> ORGANISM: Artificial sequence
<220> FEATURE:
<223> OTHER INFORMATION: Preferred spacer region

<400> SEQUENCE: 20 ttcaagaga          9

<210> SEQ ID NO 21
<211> LENGTH: 23

```
<212> TYPE: DNA
<213> ORGANISM: Artificial sequence
<220> FEATURE:
<223> OTHER INFORMATION: Primer

<400> SEQUENCE: 21
cccttgaacc tcctcgttcg acc                                           23

<210> SEQ ID NO 22
<211> LENGTH: 23
<212> TYPE: DNA
<213> ORGANISM: Artificial sequence
<220> FEATURE:
<223> OTHER INFORMATION: Primer

<400> SEQUENCE: 22
gagacgtgct acttccattt gtc                                           23

<210> SEQ ID NO 23
<211> LENGTH: 64
<212> TYPE: DNA
<213> ORGANISM: Artificial sequence
<220> FEATURE:
<223> OTHER INFORMATION: Oligonucleotide targeting murine p53.

<400> SEQUENCE: 23
gatccccgta catgtgtaat agctccttca agagaggagc tattacacat gtacttttg    60 gaaa                                                                64

<210> SEQ ID NO 24
<211> LENGTH: 63
<212> TYPE: DNA
<213> ORGANISM: Artificial sequence
<220> FEATURE:
<223> OTHER INFORMATION: Oligonucleotide targeting murine p53.

<400> SEQUENCE: 24
agcttttcca aaagtacatg tgtaatagct cctctcttga aggagctatt acacatgtac   60
ggg                                                                63

<210> SEQ ID NO 25
<211> LENGTH: 48
<212> TYPE: RNA
<213> ORGANISM: Artificial sequence
<220> FEATURE:
<223> OTHER INFORMATION: Predicted short hairpin RNA targeting murine
      p53.

<400> SEQUENCE: 25
guacaugugu aauagcuccu ucaagagaga gcuauuacac auguacuu                48
```

The invention claimed is:

1. A polynucleotide comprising:
   a RNA polymerase III promoter;
   a region encoding a siRNA, which comprises:
   i) a first region of from 18 to 30 nucleotides in length complementary to a target gene and a second region complementary to the first region; and
   ii) a spacer region having the sequence set forth in SEQ ID NO:20 separating the first and second regions; and
   a transcriptional termination element comprising five consecutive thymine residues in the sense strand of the polynucleotide,
   wherein the RNA transcript generated from the polynucleotide comprises two consecutive uridine residues immediately 3' of the second region and is capable of forming a stem-loop structure.

2. The polynucleotide of claim 1, wherein the promoter is the RNA polymerase III H1-RNA gene promoter.

3. The polynucleotide according to claim 1, wherein the promoter is an RNA polymerase III 5S, U6, adenovirus VA1, Vault, telomerase RNA, or tRNA gene promoter or a functional derivative thereof.

4. The polynucleotide of claim 1, wherein the region complementary to the target gene is front nineteen to twenty-one bases in length.

5. The polynucleotide of claim 1, wherein the step loop structure formed by the RNA transcript generated from the polynucleotide can be cleaved by an enzyme to generate a siRNA molecule with 3' overhangs at each of its termini each comprising two uridine residues.

6. The polynucleotide of claim 1, wherein the target gene is Cdh1, p53 or CDC20.

7. The polynucleotide of claim 1, wherein the siRNA is capable of discriminating between different alleles of the same gene.

8. A vector comprising the polynucleotide of claim 1.

9. An isolated cell comprising the polynucleotide of claim 1.

10. The cell according to claim 9, wherein the polynucleotide; is integrated into the cell genome.

11. A kit comprising the polynucleotide of claim 1, and a means for detecting and/or quantifying the expression of the target gene.

12. The polynucleotide of claim 1, wherein the region encoding the siRNA comprises the sequence set forth in SEQ ID NO:26.

13. A kit comprising the vector of claim 8, and a means for detecting and/or quantifying the expression of the target gene.

14. A kit comprising the cell of claim 9 or 10, and a means for detecting and/or quantifying the expression of the target gene.

15. An isolated cell comprising the vector of claim 8.

16. The cell claim 15, wherein the vector is integrated into the cells genome.

* * * * *